US010383886B2

(12) United States Patent
Addington et al.

(10) Patent No.: US 10,383,886 B2
(45) Date of Patent: Aug. 20, 2019

(54) METHOD OF TREATING NEUROLOGICAL CONDITIONS WITH OLEANDRIN

(71) Applicant: PHOENIX BIOTECHNOLOGY, INC., San Antonio, TX (US)

(72) Inventors: Otis C. Addington, San Antonio, TX (US); Robert A. Newman, Surry, ME (US)

(73) Assignee: PHOENIX BIOTECHNOLOGY, INC., San Antonio, TX (US)

( * ) Notice: Subject to any disclaimer, the term of this patent is extended or adjusted under 35 U.S.C. 154(b) by 173 days.

(21) Appl. No.: 15/704,121

(22) Filed: Sep. 14, 2017

(65) Prior Publication Data

US 2018/0000852 A1 Jan. 4, 2018

Related U.S. Application Data

(63) Continuation-in-part of application No. 15/143,973, filed on May 2, 2016, which is a continuation of application No. 13/909,613, filed on Jun. 4, 2013, now Pat. No. 9,358,293, which is a continuation of application No. 12/987,693, filed on Jan. 10, 2011, now Pat. No. 8,481,086, said application No. 15/143,973 is a continuation of application No. 13/909,652, filed on Jun. 4, 2013, now Pat. No. 8,893,965, which is a continuation of application No. 12/987,693, filed on Jan. 10, 2011, now Pat. No. 8,481,086.

(60) Provisional application No. 61/293,812, filed on Jan. 11, 2010.

(51) Int. Cl.

| A61K 36/00 | (2006.01) |
|---|---|
| A61K 31/704 | (2006.01) |
| A61K 31/7048 | (2006.01) |
| A61K 45/06 | (2006.01) |
| A61K 36/24 | (2006.01) |
| G01N 33/50 | (2006.01) |

(52) U.S. Cl.
CPC ........ *A61K 31/704* (2013.01); *A61K 31/7048* (2013.01); *A61K 36/24* (2013.01); *A61K 45/06* (2013.01); *G01N 33/5088* (2013.01); *G01N 2800/2821* (2013.01); *G01N 2800/2835* (2013.01); *G01N 2800/2871* (2013.01); *G01N 2800/52* (2013.01)

(58) Field of Classification Search
CPC .................................................... A61K 36/00
See application file for complete search history.

(56) References Cited

U.S. PATENT DOCUMENTS

| 5,977,174 A | 11/1999 | Bradley |
|---|---|---|
| 6,217,874 B1 | 4/2001 | Johannsen |
| 7,402,325 B2 | 7/2008 | Addington |
| 8,187,644 B2 | 5/2012 | Addington |
| 8,394,434 B2 | 3/2013 | Addington |
| 8,481,086 B2 | 7/2013 | Addington |
| 9,011,937 B2 | 4/2015 | Addington |
| 9,220,778 B2 | 12/2015 | Addington |
| 9,358,293 B2 | 6/2016 | Addington |
| 2006/0135443 A1 | 6/2006 | Khodadoust |
| 2006/0234955 A1 | 10/2006 | Pollard |
| 2007/0154573 A1 | 7/2007 | Rashan |
| 2007/0249711 A1 | 10/2007 | Choi |
| 2008/0200401 A1 | 8/2008 | Addington |
| 2013/0267475 A1 | 10/2013 | Addington |
| 2015/0283191 A1 | 10/2015 | Addington |
| 2016/0243143 A1 | 8/2016 | Addington |
| 2017/0274031 A1 | 9/2017 | Addington |

FOREIGN PATENT DOCUMENTS

| CN | 1301774 A1 | 2/2016 |
|---|---|---|
| EP | 2260851 A1 | 12/2010 |
| WO | 9932097 A2 | 7/1999 |
| WO | 0064921 A2 | 11/2000 |
| WO | 03099011 A1 | 12/2003 |
| WO | 2009/064657 A1 | 5/2009 |

OTHER PUBLICATIONS

Sharma et al (Sharma et al, Toxic or tonic: unexploited and emerging potential of Nerium species. Hamdard Medicus (2008), vol. 51, No. 3, pp. 171-176) (Year: 2008).*
Bai et al. ("Studies on Chemical Constituents of Japanese Nerium indicum Mill and Their Cytotoxicity in vitro" in J. Anhui Agri. SGi. (2009), 37(20), 9480-9488).
Wang et al. ("LC/MS/MS Analyses of an Oleander Extract for Cancer Treatment" in Anal. Chem. (2000), 72, 3547-3552).
Wang et al. ("Cardiac glycosides provide neuroprotection against ischemic stroke: discovery by a brain slice-based compound screening platform"). Proc. Natl. Acad. Sci. (Jul. 5, 2006), 103:27, pp. 10461-10466.
Yu et al. ("New Polysaccharide from Nerium indicum protects neurons via stress kinase signaling pathway") Brain Research, (2007), 1153, pp. 221-230.
Rodan et al. ("Stroke recurrence in children with congenital heart disease", Annals of Neurology (Jul. 2012), 72(1), 103-111).
Riikonen et al. ("Hereditary and acquired risk factors for childhood stroke", Neuropediatrics (Oct. 1994), 25(5), 227-233).
Dominiczak et al. ("Genetics of common polygenic stroke". Nature Genetics (Oct. 2003), 35(2), 116-117).
Grubb et al. ("Risks of stroke and current indications for cerebral revascularization in patients with carotid occlusion", Neurosurgery Clinics of North America (Jul. 2001), 12(3), 473-487).
Jensen et al. ("The promise and potential pitfalls of serum biomarkers for ischemic stroke and transient ischemic attack", The Neurologist (Jul. 2008), 14(4), 243-6).

(Continued)

*Primary Examiner* — Qiuwen Mi
(74) *Attorney, Agent, or Firm* — Innovar, L.L.C.; Rick Matos

(57) ABSTRACT

A method of treating neurological condition in a subject by administration of a cardiac glycoside is provided. Alzheimer's disease, Huntington's disease or stroke are treated by administering a therapeutically effective amount of cardiac glycoside, and optionally triterpene(s), to a subject. The cardiac glycoside can be present in a dosage form.

32 Claims, 11 Drawing Sheets

(56) References Cited

OTHER PUBLICATIONS

Lasek-Bal et al. ("Cardiogenic stroke in the young", Postepy w Kardiologii Inerwencyjnej (2012), 8(2), 131-137).

Rizos et al. ("Evolution of stroke diagnosis in the emergency room—a prospective observational study", Cerebrovascular diseases (Basel, Switzerland), (2009), 28(5), 448-453).

Siddiqui et al. ("Oleanderol, a new pentacyclic triterpene from the leaves of Nerium oleander", J. Natur. Prod. (1988), 51(2), 229-233).

Jaeger et al. ("Pentacyclic triterpene distribution in various plants—rich sources for a new group of multi-potent plant extracts", Molecules (2009), 14(6), 2016-2031).

Karawya et al. ("Phytochemical study of Nerium oleander growing in Egypt. Preliminary investigation", United Arab Republic J. Pharm. Sci. (1970), 11(2), 193-209.

Lo et al. ("Dual activities of the anti-cancer drug candidate PBI-05204 provide neuroprotection in brain slice models for neurodegenerative diseases and stroke", Scientific Reports (2016), 6, 25626; doi:10.1038/srep25626).

Rong et al. ("Protective effects of oleanolic acid on cerebral ischemic damage in vivo and $H_2O_2$-induced injury in vitro"; Pharm. Rio. (2011), 49(1), 78-85) (abstract).

So et al. ("Anti-ischemic activities of aralia cordata and its active component, oleanolic acid"; Arch. Pharm. Res. (2009), 32(6), 923-932) (abstract).

Li et al. ("Ursolic acid promotes the neuroprotection by activating Nrf2 pathway after cerebral ischemia in mice"; Brain Res. (2013), 1497, 32-39) (abstract).

Garcia-Morales et al. ("Anti-inflammatory, antioxidant and anti-acetylcholinesterase activities of Bouvardia temifolia: potential implications in Alzheimer's disease"; Arch. Pharm. Res. (2015), 38(7), 1369-1379).

Zhang et al. ("Ursolic acid reduces oxidative stress to alleviate early brain injury following experimental subarachnoid hemorrhage"; Neuroscience Letters (2014), 579, 12-17) (abstract).

Qian et al. ("Maslinic acid, a natural triterpenoid compound from Olea europaea, protects cortical neurons against oxygen-glucose deprivation-induced injury"; Eur. J. Pharmacol. (2011), 670(1), 148-153).

Yoo et al. ("Terpenoids as potential anti-Alzheimer's disease therapeutics"; Molecules (2012), 17(3), 3524-3538) (abstract).

Heo et al. ("Ursolic acid of *Origanum majorana* L. reduces Abeta-induced oxidative injury"; Mol. Cells (2002), 13(1), 5-11).

Chung et al. ("Inhibitory effect of ursolic acid purified from *Origanum majoma* L. on the acetylcholinesterase"; Mol. Cells (2001), 11(2), 137-143).

\* cited by examiner

Non-stroke: Oleandrin, Run 1

Non-stroke: Oleandrin, Run 2

Non-stroke: Oleandrin, Run 3

METHOD OF TREATING NEUROLOGICAL CONDITIONS WITH OLEANDRIN

CROSS-REFERENCE TO EARLIER FILED APPLICATION

The present application claims the benefit of and is a continuation-in-part of U.S. application Ser. No. 15/143,973 filed May 2, 2016, which claims the benefit of and is a continuation of U.S. application Ser. No. 13/909,652, filed Jun. 4, 2013, now U.S. Pat. No. 9,220,778 B2, issued Dec. 29, 2015, and a continuation of, U.S. application Ser. No. 13/909,613, filed Jun. 4, 2013, both of which are continuations of U.S. application Ser. No. 12/987,693 filed Jan. 10, 2011, now U.S. Pat. No. 8,481,086 B2, issued Jul. 9, 2013, which claims the benefit of U.S. Provisional Application No. 61/293,812 filed Jan. 11, 2010, the entire disclosures of which are hereby incorporated by reference.

FIELD OF THE INVENTION

The present invention concerns a method of treating neurological conditions with cardiac glycoside compounds or preparations containing them. In particular, the invention concerns a method for treating neurological disease or disorder by administration of a neuroprotective composition comprising a mixture of cardiac glycoside and at least one triterpene to a subject in need thereof.

BACKGROUND OF THE INVENTION

Neurological diseases and disorders affect brain function. Many efforts have been made to develop curative or ameliorative therapies for these diseases and disorders; however, no comprehensive or universally curative therapy has been developed, even though there are numerous pharmacotherapeutic approaches that have been proven to be effective against various different diseases and disorders.

Huntington's disease (HD) is an inherited disease of the brain that affects the nervous system. It is caused by a defective gene that is passed from parent to child. The HD gene interferes with the manufacture of a particular protein known as 'huntington' which appears to be crucial for proper brain development. The classic signs of HD include emotional, cognitive and motor disturbances. Huntington's is characterized by jerky involuntary movements (chorea), but sometimes causes rigidity without abnormal movements, changes in using the limbs (apraxia), loss of control of bodily functions and dementia, including a progressive deterioration of memory, speed of thought, judgment, and lack of awareness of problems and planning. There is no known cure for Huntington's disease. Although there are a number of medications to help control symptoms associated with HD such as emotional and movement problems, there is no treatment to stop or reverse the course of the disease. Huntington's disease has been recognized as a disease with a general membrane abnormality. A significantly elevated level and activity (10 fold increase) of Na,K-ATPase has been observed in membranes of erythrocytes and basal ganglia of Huntington's patients compared to that of normal (Butterfield D A, Oeswein J Q, Prunty M E, Hisle K C, Markesbery W R). Increased sodium, potassium adenosine triphosphatase activity in erythrocyte membranes in Huntington's disease. Ann Neurology, 4:60-62, 1978) fibroblast membranes obtained from the skin of Huntington's disease patients (Schroeder F, Goetz I E, Roberts E, Membrane anomalies in Huntington's disease fibroblasts. *J. Neurochem.* 43: 526-539, 1984).

Alzheimer's disease is a form of dementia—a neurodegenerative disease that damages the brain's intellectual functions (memory, orientation, calculation, etc.), but usually preserves its motor functions. In Alzheimer's disease, the mind gradually deteriorates, causing memory loss, confusion, disorientation, impaired judgment and other problems that may affect a person's ability to perform normal daily activities. The type, severity, sequence and progression of mental changes vary greatly. There is no known cure for Alzheimer's disease and no known way to slow its progression. For some people in the early or middle stages of the disease, medication such as tacrine may alleviate some cognitive symptoms. Aricept (donepezil) and Exelon (rivastigmine) are reversible acetylcholinesterase inhibitors that are indicated for the treatment of mild to moderate dementia of the Alzheimer's type. These drugs (called cholinesterase inhibitors) work by increasing the brain's levels of the neurotransmitter acetylcholine, helping to restore communication between brain cells. Some medications may help control behavioral symptoms such as sleeplessness, agitation, wandering, anxiety, and depression. These treatments are aimed at making the patient more comfortable. Although no medication is known to cure Alzheimer's disease, cholinesterase inhibitors may improve performance of daily activities, or lessen behavioral problems. Medications for the treatment of Alzheimer's disease currently being tested include oestrogens, nonsteroidal anti-inflammatory agents, vitamin E, selegiline (Carbex, Eldepryl) and the botanical product gingko biloba.

Under normal conditions, neurons maintain their testing membrane potential and function regulated by membrane-bound, homeostatic, energy-dependent Na—K-ATPase pumps. Ischemia triggers alterations in ion homeostatsis potentially leading to irreversible tissue injuries. Compromised Na,K-ATPase activity has been suggested to play a role in a neuropathologic and apoptotic process in some models of focal ischemia and traumatic brain injury. The role of Na,K-ATPase in stroke-mediated ischemic brain injury has been reported to be associated with several different molecular mechanisms. Inhibition of Na,K-ATPase catalytic activity can, for example, lead to a reduction of ATP consumption during ischemia-reperfusion. Additionally, the deletion of cytosolic $Ca^{2+}$ may cause neuronal cell death. Thus, inhibition of Na,K-ATPase, such as by cardiac glycosides, may result in an increase in intracellular $Ca^{2+}$ levels and a decline in extrusion of intracellular $Ca^{2+}$ via the Na—Ca exchanger. In line with this, the relatively lower levels of intracellular $Ca^{2+}$ in hippocampal CA1 neurons has been observed three days after transient ischemia and elevation of calcium levels is believed to provide protection against delayed neuronal death across a wide range of post-ischemic treatment times.

One of the pharmacological mechanisms of action of cardiac glycosides involves their ability to bind to the ion exchange pump, Na, K-ATPase and to inhibit the activity of this particular enzyme. Na, K-ATPase, the transmembrane protein that catalyzes the active transport of $Na^+$ and $K^+$ across the plasma membrane, is a well established pharmacologic receptor for cardiac glycosides. This enzyme hydrolyzes ATP and uses the free energy to drive transport of $K^+$ into the cell and $Na^+$ out of cells, against their electrochemical gradients (Hauptman, P. J., Garg, R., and Kelly, R. A. Cardiac glycosides in the next millennium. *Prog. Cardiovasc. Dis.* 41: 247-254, 1999).

Na, K-ATPase is composed of two heterodimer subunits, the catalytic α-subunit and the glycosylated β-subunit. There is also a γ subunit, but it has not been studied in detail. The α-subunit has binding sites for ATP, $Na^+$, $K^+$, and cardiac glycosides. The β-subunit functions to stabilize the catalytic α-subunit and may play a regulatory role as well. Four different α isoforms (α1, α2, α3, α4) and three different β isoforms (β1, β2, and β3) have been identified in mammalian cells. The relative expression of each subunit type is markedly altered in normal and diseased states. Additionally, the apparent affinity of cardiac glycosides to the different α isoforms is quite different. Binding of cardiac glycosides to the α1 isoform is less than that which occurs with the α2 and α3 isoforms which are 250-fold or higher more sensitive to inhibition by this type of drug (Blanco, G. and Mercer, R. W. Isozymes of the Na, K-ATPase: heterogeneity in structure, diversity in function. Am. J. Physiol. 275 (Renal Physiol. 44): F633-F650, 1998). Sakai et al. (FEBS Letters 563: 151-154, 2004) report that expression of the α3 subunit isoform is increased in human colorectal cancer cells as compared to normal colorectal cells.

There is a broad range in relative water as opposed to lipid solubility of cardiac glycosides. While most cardiac glycosides can bind to and inhibit Na,K-ATPase activity, those cardiac glycosides which are relatively more water soluble (hydrophilic) than lipid soluble (lipophilic or hydrophobic) have only a limited ability to cross the lipid barrier to the brain known as the blood-brain barrier. The blood-brain barrier (BBB) is a separation of circulating blood and cerebrospinal fluid (CSF) maintained by the choroid plexus in the central nervous system (CNS). Endothelial cells restrict the diffusion of microscopic objects (e.g. bacteria) and large or hydrophilic molecules into the CSF, while allowing the diffusion of small hydrophobic molecules ($O_2$, hormones, lipid soluble cardiac glycosides, etc)

*Nerium oleander* is an ornamental plant widely distributed in subtropical Asia, the southwestern United States, and the Mediterranean. Its medical and toxicological properties have long been recognized. It has been used, for example, in the treatment of hemorrhoids, ulcers, leprosy, snake bites, and even in the induction of abortion. Oleandrin, an important component but not the sole component of oleander extract, is a cardiac glycoside.

Extraction of glycosides from plants of *Nerium* species has provided pharmacologically/therapeutically active ingredients from *Nerium oleander*. Among these are oleandrin, neriifolin, and other cardiac glycoside compounds. Oleandrin extracts obtained by hot-water extraction of *Nerium oleander*, sold under the trademark ANVIRZEL™, contain the concentrated form or powdered form of a hot-water extract of *Nerium oleander*. A Phase I trial of a hot water oleander extract (i.e. Anvirzel™) has been completed (Mekhail et al., *Am. Soc. Clin. Oncol.*, vol. 20, p. 82b, 2001). It was concluded that oleander extracts, which would provide about 57 ug oleandrin/day, can be safely administered at doses up to 1.2 ml/m²/d. No dose limiting toxicities were found.

Huachansu is an extract obtained from toad skin and it comprises bufadienolides, such as bufalin, a cardiac glycoside. HuaChanSu is an approved medication for the treatment of cancer in China. It has been used to treat various cancers, including hepatic, gastric, lung, skin, and esophageal cancers.

Rong et al. (Pharm. Biol. (January 2011), 49(1), 78-85) suggest oleanolic acid might be suitable for attenuating ischemic stroke. So et al. (Arch. Pharm. Res. (June 2009), 32(6), 923-932) suggest oleanolic acid might be suitable for the prevention and treatment of neurodegeneration in stroke. Li et al. (Brain Res. (February 2013), 1497, 32-39) suggest ursolic acid might provide neuroprotection after cerebral ischemia in mice. Garcia-Morales et al. (Arch. Pharm. Res. (July 2015), 38(7), 1369-1379) suggest that an extract of *Bouvardia ternifolia* should be further studied for treating Alzheimer's disease. Zhang et al. (Neuroscience Letters (2014), 579, 12-17) report that ursolic acid reduces oxidative stress following experimental subarachnoid hemorrhage. Qian et al. (Eur. J. Pharmacol. (2011), 670, 148-153) report that maslinic acid protects cortical neurons against oxygen-glucose deprivation-induced injury in rats. EP 2260851 A1 to Consejo Superior de Investigaciones Cientificas (Madrid, E S) suggests the use of oleanolic acid for the treatment of multiple sclerosis. Yoo et al. (Molecules, (May 2012), 17(3), 3524-38) suggest the use of terpenoids as anti-Alzheimer's disease therapeutics. Heo et al. (Mol. Cells (February 2002), 13(1), 5-11) suggest ursolic acid reduces amyloid beta protein-induced oxidative cell death. Chung et al. (Mol. Cells (April 2001), 11(2), 137-143) suggest ursolic acid appears to be a potent inhibitor of acetylcholinesterase in Alzheimer's disease. US 2007/0249711 A1 (Pub. Date. Oct. 25, 2007) to Choi et al. suggests the use of oleanolic acid and ursolic acid for improving brain functions to prevent and treat mild cognitive impairment and dementia.

None of the art suggests neuroprotective compositions comprising (or consisting essentially of) a combination of cardiac glycoside and at least one, at least two or at least three triterpenes selected from oleanolic acid, ursolic acid and betulinic acid, nor use of such a composition for the treatment of neurological conditions.

SUMMARY OF THE INVENTION

The invention provides a method of treating a neurological condition comprising administering to a subject in need thereof a neuroprotective composition comprising a cardiac glycoside in an effective amount to treat said neurological condition or comprising at least one cardiac glycoside and at least one triterpene together being present in an effective amount to treat said neurological condition.

Another aspect of the invention provides a method of treating, in a subject in need thereof, a neurological disease or disorder having an etiology associated with altered Na,K-ATPase activity with a neuroprotective composition comprising cardiac glycoside, the method comprising:
determining that the subject has a neurological disease or disorder having an etiology associated with altered Na, K-ATPase α3 isoform to α1 isoform subunit ratio or associated with altered Na,K-ATPase activity; and
indicating administration to the subject a composition comprising cardiac glycoside.

Some embodiments of the invention include those wherein: 1) the subject is prescribed and administered a therapeutically relevant dose of composition comprising cardiac glycoside; 2) the subject is administered the composition comprising cardiac glycoside according to a prescribed dosing regimen; 3) the subject is administered a composition comprising an extract comprising a cardiac glycoside; 4) the extract further comprises one or more other therapeutically effective agents obtained along with the cardiac glycoside during extraction; 5) the composition further comprises one or more other non-cardiac glycoside therapeutically effective agents, i.e. an agent that is not a cardiac glycoside; 6) the subject is administered a hot water extract of a plant or animal source containing cardiac glycosides 2 mg to 22.5 mg per day, or a concentrated extract (e.g. supercritical $CO_2$ extract or organic solvent extract) of a plant or animal source of cardiac glycosides ranging from 0.6 to 4.8 mg, or a pure single chemical form of a cardiac glycoside ranging from 10 to 500 μg or 10 to 100 μg; and/or 7) the neuroprotective composition comprises at least one cardiac glycoside and at least one triterpene. In some embodiments, the at least one triterpene is selected from the group consisting of oleanolic acid, ursolic acid, betulinic acid and salt, derivative or prodrug form(s) thereof.

The invention also provides a method of treating a neurological condition in a subject in need thereof comprising:
determining whether or not the neurological condition in the subject is Alzheimer's disease, Huntington's disease, stroke or other neurological condition;
indicating administration of a neuroprotective composition comprising at least one cardiac glycoside;
administering an initial dose of neuroprotective composition comprising at least one cardiac glycoside to the subject according to a prescribed initial dosing regimen for a period of time;
periodically determining the adequacy of subject's clinical response and/or therapeutic response to treatment with cardiac glycoside; and
if the subject's clinical response and/or therapeutic response is adequate, then continuing treatment with the at least one cardiac glycoside as needed until the desired clinical endpoint is achieved; or
if the subject's clinical response and/or therapeutic response are inadequate at the initial dose and initial dosing regimen, then escalating or deescalating the dose until the desired clinical response and/or therapeutic response in the subject is achieved.

The invention also provides a method of preventing or reducing the incidence of occurrence of a neurological condition in a population of subjects at risk thereof, the method comprising:
administering an effective dose of neuroprotective composition comprising at least one cardiac glycoside on a recurring basis for an extended period of time to one or more subjects in a population of subjects at risk of suffering from a neurological condition such as Alzheimer's disease, Huntington's disease, stroke or other neurological condition, thereby preventing or reducing the incidence of the neurological condition in the population.

The invention also includes embodiments wherein: a) the method further comprises indicating administration of cardiac glycoside to the one or more subjects; b) the method further comprises administering an effective dose of cardiac glycoside to the subject according to a prescribed dosing regimen for a period of time; c) the method further comprises periodically determining the adequacy of one or more subject's clinical response and/or therapeutic response to treatment with cardiac glycoside; d) if the subject's clinical response and/or therapeutic response is adequate, then the method further comprises continuing treatment with cardiac glycoside as needed until the desired clinical endpoint is achieved; e) if the subject's clinical response and/or therapeutic response are inadequate at the initial dose and initial dosing regimen, then the method further comprises escalating or deescalating the dose until the desired clinical response and/or therapeutic response in the subject is achieved; f) the cardiac glycoside is administered to plural subjects in a population; g) the recurring basis is daily, every other day, every second day, every third day, every fourth day, every fifth day, every sixth day, weekly, every other week, every second week, every third week, monthly, bimonthly, semi-monthly, every other month every second month, quarterly, every other quarter, trimesterly, seasonally, semi-annually and/or annually; h) the extended period is one or more weeks, one or more months, one or more quarters and/or one or more years; i) the effective dose is administered one or more times in a day; j) the method further comprises identifying a population of subjects at risk of suffering from a neurological condition such as Alzheimer's disease, Huntington's disease, stroke or other neurological condition; and/or k) the population of subjects at risk is characterized by advancing age of the subject, familial history of the neurological condition, genetic predisposition to occurrence of neurological condition, the presence and expression of ApoE4 gene in the subject, female gender (twice as many women get Alzheimer's disease than men), cardiovascular disease (e.g. high blood pressure and high cholesterol levels), diabetes (especially Type 2 or adult onset forms of this disease), Down's Syndrome, head injury, low levels of formal education, smoking, excessive alcohol consumption and/or drug abuse.

The invention also provides a time-delayed method of treating stroke in a subject comprising:
within an acceptable delay period after a subject has suffered the stroke, administering an initial dose of neuroprotective composition comprising at least one cardiac glycoside according to an initial dosing regimen;
determining the adequacy of subject's clinical response and/or therapeutic response to treatment with cardiac glycoside; and
if the subject's clinical response and/or therapeutic response is adequate, then continuing treatment with the neuroprotective composition comprising at least one cardiac glycoside as needed until the desired clinical endpoint is achieved; or
if the subject's clinical response and/or therapeutic response are inadequate at the initial dose and initial dosing regimen, then escalating or deescalating the dose until the desired clinical response and/or therapeutic response in the subject is achieved.

Some embodiments of the invention include those wherein: 1) the delay period is 10 hours or less, 8 hours or less, 6 hours or less, 4 hours or less, 3 hours or less, 2 hours or less, 1 hour or less, 45 minutes or less, 30 minutes or less, 20 minutes or less or 10 min or less; 2) determining the adequacy of a subject's clinical and/or therapeutic response is done by assessments of any weakness of the face, arm and/or leg on one side of the body, numbness in the face, arm, and/or leg on one side of the body, inability to understand spoken language, inability to speak or speak clearly, inability to write, vertigo and/or gait imbalance, double vision and an unusually severe headache; or 3) a combination thereof.

The invention also provides use of a neuroprotective composition comprising at least one cardiac glycoside in the manufacture of a medicament for the treatment of a neurological condition in a subject. In some embodiments, the manufacture of such a medicament comprises: providing at least one cardiac glycoside; including a dose of the at least one cardiac glycoside in a pharmaceutical dosage form; and packaging the pharmaceutical dosage form. In some embodiments, the manufacture can be conducted as described in PCT International Application No. PCT/US06/29061. The manufacture can also include one or more additional steps such as: delivering the packaged dosage form to a vendor (retailer, wholesaler and/or distributor); selling or otherwise providing the packaged dosage form to a subject having a neurological condition; including with the medicament a label and a package insert, which provides instructions on use, dosing regimen, administration, content and toxicology profile of the dosage form. In some embodiments, the treatment of a neurological condition comprises: determining that a subject has a neurological disease or disorder; indicating administration of cardiac glycoside to the subject according to a dosing regimen; administering to the subject one or more pharmaceutical dosage forms containing cardiac glycoside, wherein the one or more pharmaceutical dosage forms is administered according to the dosing regimen.

The invention also provides a cardiac glycoside or cardiac glycoside-containing neuroprotective composition, i.e. a pharmaceutical formulation or dosage form, for the treatment of a neurological condition. In some embodiments, the cardiac glycoside-containing neuroprotective composition comprises an extract as described herein or in U.S. Pat. No. 7,402,325 issued Jul. 22, 2008, U.S. Pat. No. 8,394,434 B2 issued Mar. 12, 2013, U.S. Pat. No. 8,187,644 B2 issued May 29, 2012, PCT International Application No. PCT/US06/29061 filed Feb. 8, 2007, and/or application No. U.S. Ser. No. 12/019,435, the entire disclosures of which are hereby incorporated by reference.

In some embodiments, the subject having a neurological condition, i.e. the subject in need thereof, is part of a population of such subjects. The invention provides a method for improving the clinical status of a statistically significant number of subjects of in a population of subjects having a neurological condition, the method comprising: administering to the population of subjects a cardiac glycoside or cardiac glycoside-containing composition; and determining the clinical status of the subjects. In some embodiments, the statistically significant number is at least 5% of the population.

In some embodiments, the neurological condition is Alzheimer's disease, Huntington's disease, stroke or other neurological condition, such as described herein. The medicament can be manufactured by inclusion of the cardiac glycoside in a pharmaceutical dosage form containing one or more pharmaceutically acceptable excipients.

Treatment of the subject with at least one cardiac glycoside is continued as needed. The dose or dosing regimen can be adjusted as needed until the patient reaches the desired clinical endpoint(s) such as a reduction or alleviation of specific neurological symptoms associated with the disease. Determination of the adequacy of clinical response and/or therapeutic response can be conducted by a clinician familiar with the neurological condition being treated.

In some embodiments, the neurological condition is selected from the group consisting of neurological disease, neurological disorder, and stroke. In some embodiments, the neurological disease is a neurodegenerative disease. In some embodiments, the neurodegenerative disease is selected from the group consisting of Huntington's disease, Alzheimer's disease, Parkinson's disease, amyotrophic lateral sclerosis, bovine spongiform encephalopathy, multiple sclerosis, diabetic neuropathy, autism and juvenile neuronal ceroid lipofuscinosis. In some embodiments, stroke is ischemic stroke or stroke-mediated ischemic injury.

In some embodiments: 1) the at least one cardiac glycoside is selected from the group consisting of oleandrin, ouabain, bufalin, digitoxin, cinobufatalin, cinobufagin, and resibufogenin; 2) the cardiac glycoside is present in pure form whether derived through extraction of a plant or animal source, synthesized or manufactured through chemical modification (e.g. derivatization) of an available cardiac glycoside; 3) the cardiac glycoside is present in an extract; 4) the cardiac glycoside is present in a pharmaceutical formulation or composition; 5) the cardiac glycoside has been obtained from an oleander plant mass; 6) the oleander plant mass comprises Nerium species, such as Nerium oleander, or of Thevetia species, such as Thevetia neriifolia (otherwise known as yellow oleander); 7) the cardiac glycoside crosses the blood brain barrier (BBB) after administration to the subject; 8) the cardiac glycoside extract was prepared by supercritical fluid (SCF) extraction optionally in the presence of a modifier; 9) the cardiac glycoside is oleandrin; 10) the cardiac glycoside has a clearance rate for brain tissue of no greater than 4 L/hr; 11) following administration thereof by any of the routes disclosed herein, the cardiac glycoside is retained in the brain tissue for a period of at least 8 hours; and/or 12) the at least one triterpene is selected from the group consisting of oleanolic acid, ursolic acid, betulinic acid and salt, derivative or prodrug form(s) thereof. In some embodiments, the cardiac glycoside excludes neriifolin.

In some embodiments: 1) the SCF extract further comprises at least one other pharmacologically active agent aside from the cardiac glycoside, said other pharmacologically active agent having been obtained along with the cardiac glycoside during the extraction process used to prepare the extract; 2) the SCF extract further comprises at least one other non-cardiac glycoside pharmacologically active agent; 3) the other pharmacologically active agent may contribute to the therapeutic efficacy of the cardiac glycoside when the extract is administered to a subject; 4) the other pharmacologically active agent functions additively or synergistically to contribute to the therapeutic efficacy of the cardiac glycoside; and/or 5) the extract has been obtained from toad skin or secretions therefrom.

In some embodiments, the neuroprotective composition consists essentially of oleandrin and at least one, at least two or at least three triterpene(s) selected from the group consisting of oleanolic acid, ursolic acid and betulinic acid. In some embodiments, the molar ratio of oleandrin to total triterpene is in the range of about 1:about 9-12, about 1:about 9-11, about 1:about 9.5-10.5, or about 1 to about 10.

In some embodiments, the neuroprotective composition comprises at least two or at least three triterpenes in addition to oleandrin. The molar ratio of oleandrin to the individual triterpenes can vary as follows for oleanolic acid, ursolic acid and betulinic acid. Approximate (±15%, ±10% or ±5% of specified value) ranges for molar ratios in neuroprotective composition:

| Composition | Oleandrin | Oleanolic acid | Ursolic acid | Betulinic acid |
| --- | --- | --- | --- | --- |
| A | 0.5-1.5 | 4-6 | — | — |
| B | 0.5-1.5 | 4-6 | 4-6 | — |
| C (PBI-05204) | 0.5-1.5 | 4-6 | 4-6 | 0.1-1 |
| D | 0.5-1.5 | — | 4-6 | — |
| E | 0.5-1.5 | — | — | 0.1-1 |
| F | 0.8-1.2 | 4-6 | — | — |
| G | 0.8-1.2 | 4-6 | 4-6 | — |
| H | 0.8-1.2 | 4-6 | 4-6 | 0.1-1 |
| J | 0.8-1.2 | — | 4-6 | — |
| K | 0.8-1.2 | — | — | 0.1-1 |
| L | 0.9-1.1 | 4-6 | — | — |
| M | 0.9-1.1 | 4-6 | 4-6 | — |
| N | 0.9-1.1 | 4-6 | 4-6 | 0.1-1 |
| P | 0.9-1.1 | — | 4-6 | — |
| Q | 0.9-1.1 | — | — | 0.1-1 |
| R | 0.9-1.1 | 4-5 | — | — |
| S | 0.9-1.1 | 4-5 | 4-5 | — |
| T | 0.9-1.1 | 4-5 | 4-5 | 0.3-0.7 |
| U | 0.9-1.1 | — | 4-5 | — |

-continued

| Composition | Oleandrin | Oleanolic acid | Ursolic acid | Betulinic acid |
|---|---|---|---|---|
| V | 0.9-1.1 | — | — | 0.3-0.7 |
| W | About 1 | 4-5 | — | — |
| X | About 1 | 4-5 | 4-5 | — |
| Y | About 1 | 4-5 | 4-5 | 0.3-0.7 |
| Z | About 1 | — | 4-5 | — |
| AA | About 1 | — | — | 0.3-0.7 |
| AB | About 1 | About 4.7 | — | — |
| AC | About 1 | About 4.7 | About 4.5 | — |
| AD (PBI-05204) | About 1 | About 4.7 | About 4.5 | About 0.6 |
| AE | About 1 | — | About 4.5 | — |
| AF | About 1 | — | — | About 0.6 |

In some embodiments, the total molar amount of triterpene is in excess over the molar amount of oleandrin in the neuroprotective composition. In some embodiments, the molar amount of oleanolic acid is four-fold to six-fold higher or five-fold to ten-fold higher or ten-fold to fifteen-fold higher or fifteen-fold to twenty-fold higher than the molar amount of oleandrin in the neuroprotective composition. In some embodiments, the molar amount of ursolic acid is four-fold to six-fold higher or six-fold to ten-fold higher or ten-fold to fifteen-fold higher than the molar amount of oleandrin in the neuroprotective composition. In some embodiments, the molar amount of betulinic acid is less than the molar amount of oleandrin in the neuroprotective composition. In some embodiments, the total molar amount of oleanolic acid and ursolic acid is eight-fold to twelve-fold higher or twelve-fold to fifteen-fold higher than the molar amount of oleandrin in the neuroprotective composition. In some embodiments, the total molar amount of oleanolic acid and betulinic acid is four to seven-fold higher than the molar amount of oleandrin in the neuroprotective composition. In some embodiments, the total molar amount of ursolic acid and betulinic acid is four to seven-fold higher than the molar amount of oleandrin in the neuroprotective composition. In some embodiments, the total molar amount of oleanolic acid, ursolic acid, and betulinic acid together is eight to thirteen-fold higher, nine to twelve-fold higher, nine to eleven-fold higher, nine to ten-fold higher, about 9.5 to about 10.5-fold higher, or about 10-fold higher than the molar amount of oleandrin in the neuroprotective composition.

Methods described herein will therapeutically effective amounts of neuroprotective compositions described herein.

In some embodiments, the neurological condition has an etiology associated with specific changes in Na,K-ATPase activity either through increased enzyme activity such as that associated with juvenile autism (Clin. Biochem. 2009; 42(10-11), 949-957), decreased enzyme activity such as that observed in diabetic neuropathy (Neuroscience 2009), Batten disease (Exp. Cell Res. 2008, 314(15):2895-2905), age-related dementia and Alzheimer's disease (J. Alzheimers Dis. 2008, 14(1): 85-93; Neurobiol. Aging 2007, 28(7):987-994), or specific mutations in Na,K-ATPase subunit structure such as that associated with Parkinson's disease (Human Gen. 2009, 126(3):431-447).

The individual steps of the methods of the invention can be conducted at separate facilities or within the same facility.

In some embodiments, the neurons are in vitro, ex vivo or in vivo. In some embodiments, the neurons are CA-1 neurons.

The invention also provides: a method of treating a neurological condition; a method of treating, in a subject in need thereof, a neurological disease or disorder having an etiology associated with altered Na,K-ATPase activity; use of a cardiac glycoside in the manufacture of a medicament for the treatment of a neurological condition; and/or a cardiac glycoside or cardiac glycoside-containing neuroprotective composition for the treatment of a neurological condition substantially as shown and described herein.

The invention includes all combinations of the aspects, embodiments and sub-embodiments of the invention disclosed herein.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

FIG. 7A depicts a concentration-response curve showing the relation for oleandrin (gray filled circles). A compendium of 6 runs normalized to the difference between internal positive (non-OGD) and negative (OGD) controls for each run set to 100%; means±SEM are shown. The concentration relation for neriifolin (open squares) is reprinted here as taken from Wang et al. (Proc. Natl. Acad. Sci. USA (2006), 103(27), 10461-10466) for comparison. FIG. 7B depicts a concentration response curve showing the relation for PBI-05204 (black filled squares). A compendium of 13 runs normalized to the difference between internal positive (non-OGD) and negative (OGD) controls for each run set to 100%; means±SEM are shown. Data from FIG. 7A for oleandrin are replotted in FIG. 7B assuming a 3% composition for oleandrin in the PBI-05204 extract.

DETAILED DESCRIPTION OF THE INVENTION

Figure 1A:
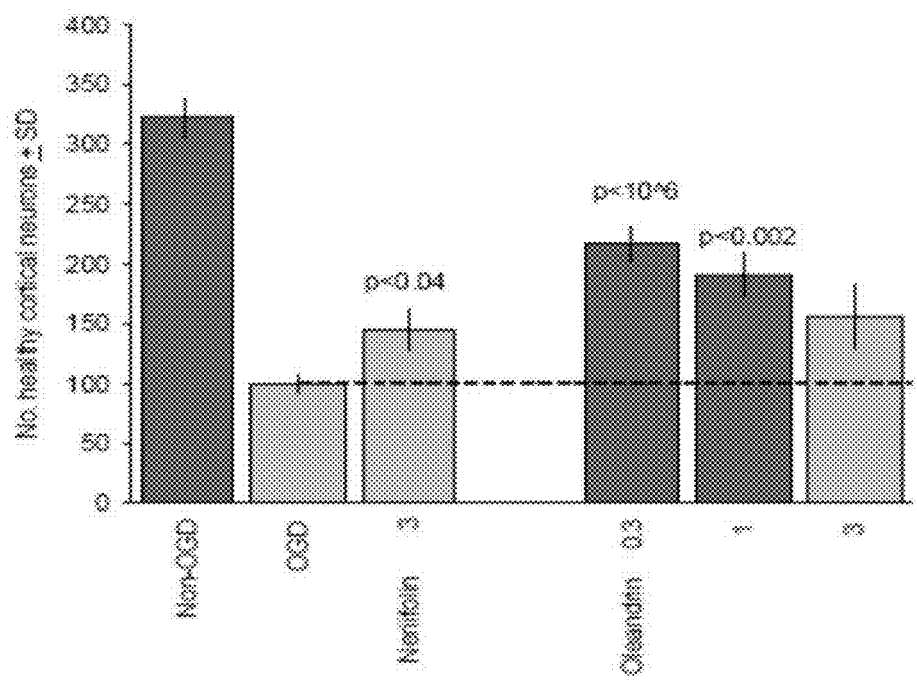
FIGS. 1A-1C depict results of the comparative evaluation of oleandrin versus neriifolin in a neuroprotection brain-slice-based "stroke" assay (Example 8), wherein the number of healthy cortical neurons is determined following 5-6 minutes of oxygen and glucose deprivation (OGD) in the presence or absence of those agents. The results of three independent experiments are presented.

As used herein, the generic terms triterpene and cardiac glycoside also encompass salts and derivatives thereof, unless otherwise specified. A triterpene may also be present in its free acid form.

The invention provides a method of treating a neurological condition by administration of an effective dose of neuroprotective composition comprising at least one cardiac glycoside to a subject in need thereof. The neuroprotective composition comprising at least one cardiac glycoside is administered according to a dosing regimen best suited for the subject, the suitability of the dose and dosing regimen to be determined clinically according to conventional clinical practices and clinical treatment endpoints for the neurological condition being treated.

In some embodiments, the neurodegenerative disorder or neurological condition being treated has an etiology associated with Na,K-ATPase binding activity or with disregulation of Na,K-ATPase within a cell or tissue. In some embodiments, the neurodegenerative disorder or neurological condition being treated has an etiology associated with HIF-1α binding activity or with disregulation of HIF-1α within a cell or tissue. Such disregulation may occur, for example, as a significant alteration in the extent of enzymatic activity. This, in turn, may result from a change in enzyme function, enzyme content or even distribution within an affected tissue.

A subject treated according to the invention will exhibit a therapeutic response. By "therapeutic response" is meant that a subject suffering from the disease or disorder will enjoy at least one of the following clinical benefits as a result of treatment with a neuroprotective composition comprising at least one cardiac glycoside: amelioration of the disease or disorder, reduction in the occurrence of symptoms associated with the disease or disorder, partial remission of the disease or disorder, full remission of the disease or disorder, or increased time to progression. In other words, the therapeutic response can be a full or partial therapeutic response.

A therapeutic response can also be described as one in which the quality of life of the patient afflicted with the neurodegenerative disease is improved. Improvement in quality of life may occur, for example, through a reduction in occurrence, frequency or severity of symptoms associated with the disease (e.g. tremors, involuntary muscle movements, loss or partial loss of nerve-muscle coordination, memory retention, etc.).

"Preventing occurrence of a neurological condition in a population of subjects at risk" means that the neurological condition will not occur during a predetermined time period in a demographically predetermined population of subjects that are at risk of suffering from the neurological condition. The prevention during the predetermined time period occurs as a result of subjects in that population having been administered a neuroprotective composition comprising at least one cardiac glycoside according to the methods of the invention. As one example, when a neuroprotective composition comprising at least one cardiac glycoside-containing composition is administered for a predetermined time period to subjects in a population of subjects at risk of suffering from stroke, stroke will not occur in those subjects during the predetermined time period. In particular, a neuroprotective composition comprising at least one cardiac glycoside-containing composition is chronically administered over a period of one year to a population of subjects at risk of suffering from Alzheimer's disease, and the subjects in that population do not exhibit symptoms associated with Alzheimer's during that one-year period.

"Reducing the incidence of occurrence of a neurological condition in a population of subjects at risk" is related in meaning to "preventing the incidence", except that "reducing the incidence of occurrence" permits the occurrence of the neurological condition in a demographically predetermined population of subjects but at a rate of occurrence or a level of severity that is reduced as compared to an otherwise demographically similar predetermined population of subjects at risk not being administered the cardiac glycoside-containing composition according to the methods of the invention.

As used herein, "time to progression" is the period, length or duration of time after a disease is diagnosed (or treated) until the disease begins to worsen. It is the period of time during which the level of a disease is maintained without further progression of the disease, and the period of time ends when the disease begins to progress again. Progression of a disease is determined by "staging" a subject suffering from a neurological condition prior to or at initiation of therapy. For example, the subject's neurological health is determined prior to or at initiation of therapy. The subject is then treated with neuroprotective composition comprising at least one cardiac glycoside, and the neurological health monitored periodically. At some later point in time, the symptoms of the neurological condition may worsen, thus marking progression of the disease and the end of the "time to progression". The period of time during which the disease did not progress or during which the level or severity of the disease did not worsen is the "time to progression".

A dosing regimen includes a therapeutically relevant dose (or effective dose) of neuroprotective composition comprising one or more cardiac glycosides administered according to a dosing schedule. A therapeutically relevant dose, therefore, is a therapeutic dose at which a therapeutic response of the disease or disorder to treatment with a cardiac glycoside is observed and at which a subject can be administered the cardiac glycoside without an excessive amount of unwanted or deleterious side effects. A therapeutically relevant dose is non-lethal to a subject, even though it may cause some side effects in the patient. It is a dose at which the level of clinical benefit to a subject being administered the cardiac glycoside exceeds the level of deleterious side effects experienced by the subject due to administration of the cardiac glycoside. A therapeutically relevant dose will vary from subject to subject according to a variety of established pharmacologic, pharmacodynamic and pharmacokinetic principles. However, a therapeutically relevant dose (relative, for example, to oleandrin) will typically not exceed 25 micrograms, 75 micrograms, 100 micrograms/day, 150 micrograms/day, 200 micrograms/day, 225 micrograms/day, 250 micrograms/day, 300 micrograms/day, or 500 micrograms/day of cardiac glycoside or it can be in the range of 25-500 micrograms/day or 25-300 micrograms/day of cardiac glycoside. It is known in the art that the actual amount of a drug required to provide a target therapeutic result in a subject may vary from subject to subject according to the basic principles of pharmacy.

A therapeutically relevant dose can be administered according to any dosing regimen typically used in the treatment of neurological or neurodegenerative diseases or disorders. A therapeutically relevant dose can be administered once, twice, thrice or more daily dosing schedule. It can be administered every other day, every third day, every fourth day, every fifth day, semiweekly, weekly, biweekly, every three weeks, every four weeks, monthly, bimonthly, semimonthly, every three months, every four months, semi-annually, annually, or according to a combination of any of the above to arrive at a suitable dosing schedule. For example, a therapeutically relevant dose can be administered once daily for one or more weeks.

The examples below include evidence of the efficacy of cardiac glycosides in neurological conditions such as neurological diseases, neurological disorders and stroke. Example 3 details a method of treating Alzheimer's disease with neuroprotective composition comprising at least one cardiac glycoside or a combination of cardiac glycoside with one or more other therapeutic agents. Example 4 details a method of treating Huntington's disease with cardiac glycoside or a combination of cardiac glycoside with one or more other therapeutic agents. Example 5 details a method of treating stroke-mediated ischemic brain injury with cardiac glycoside or a combination of cardiac glycoside with one or more other therapeutic agents.

In general, a subject having a neurological condition is treated as follows. A subject presenting with a neurological condition is evaluated to determine whether or not the neurological condition is Alzheimer's disease, Huntington's disease, stroke or other neurological condition. Administration of cardiac glycoside is indicated. Initial doses of cardiac glycoside are administered to the subject according to a prescribed dosing regimen for a period of time. The subject's clinical response and level of therapeutic response are determined periodically. If the level of therapeutic response is too low at one dose, then the dose is escalated according to a predetermine dose escalation schedule until the desired level of therapeutic response in the subject is achieved. Treatment of the subject with cardiac glycoside is continued as needed. The dose or dosing regimen can be adjusted as needed until the patient reaches the desired clinical endpoint(s) such as cessation of the disease itself, reduction in disease associated symptoms, and/or a reduction in the progression of the disease process.

Figure 1B:
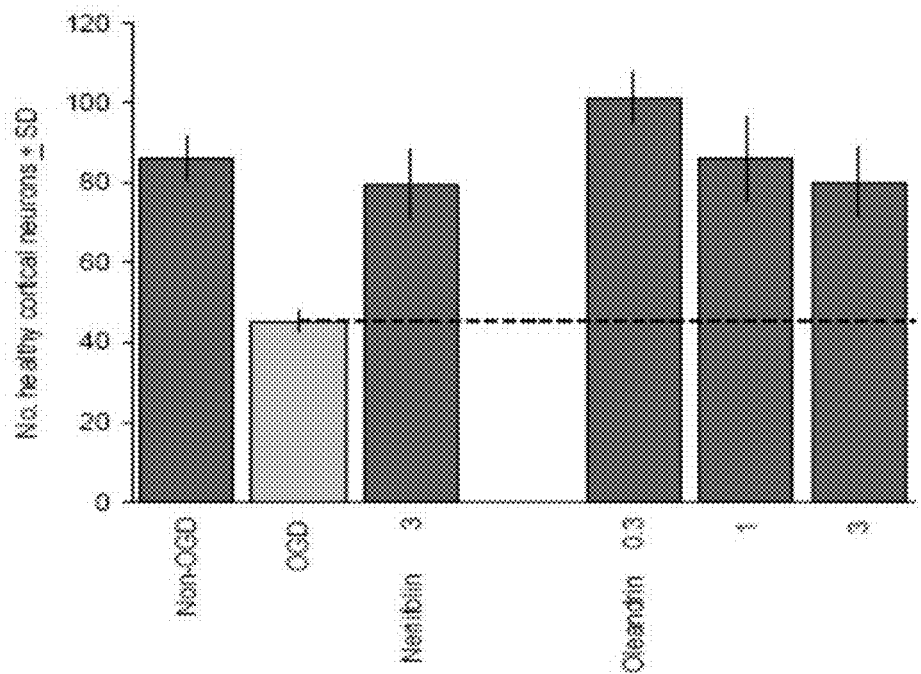
Figure 1C:
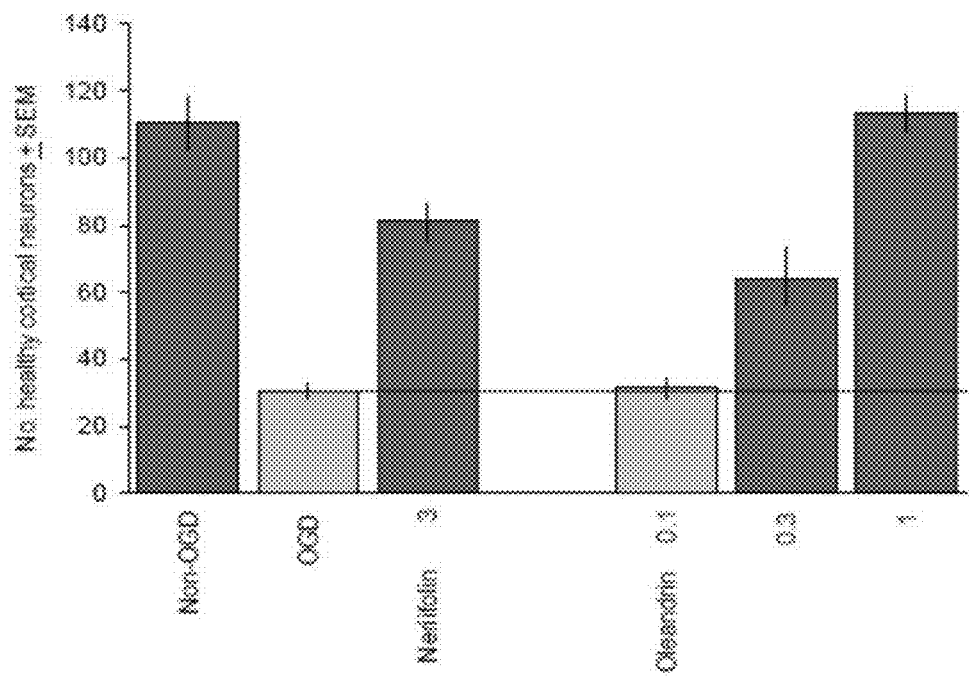

Example 8 provides a detailed description of an in vitro assay used to evaluate the efficacy of the cardiac glycosides for the treatment of stroke-mediated ischemic neuronal injury. The assay is a brain slice-based assay for oxygen and glucose deprivation (OGD) used to induce ≥50% loss of healthy cortical neurons by 24 hours. The cardiac glycoside Neriifolin (3 µM) is used as a positive control. Oleandrin was tested in OGD treated brain slices (stroke model, FIGS. 1A-1C) and non-OGD treated brain slices (non-stroke model, FIGS. 2A-2C). The data indicate that oleandrin provides substantial neuroprotection when the brain slices (neurons) are exposed to solutions of oleandrin ranging in concentration from 0.1 to 3 µM. While no direct measurements have been made in human brain following a systemic dose of oleandrin, it can be assumed from data obtained in a phase I study of oleander extract as well as data previously obtained in rodent studies in which the ability of oleandrin to specifically cross the blood brain barrier was examined that a dose level to reach this concentration of oleandrin in the human brain would be probably around 1-10 ng, about 3-6 ng, or about 4 ng.

Figure 1D:
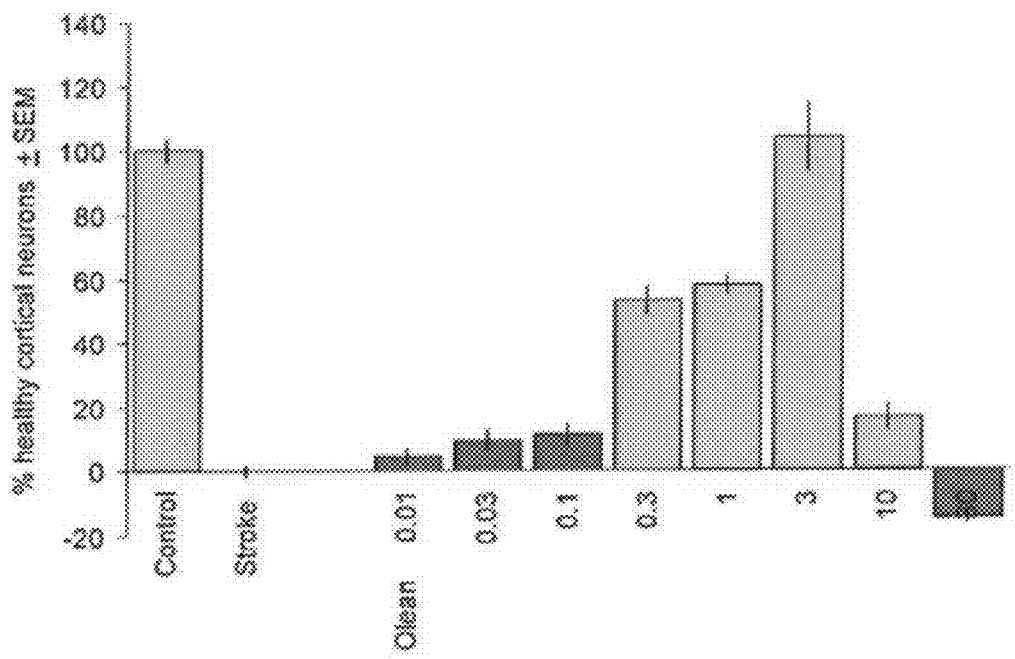
FIG. 1D depicts concentration-response data obtained from the comparative evaluation of the oleandrin versus neriifolin, the control, in a neuroprotection brain-slice-based "stroke" assay (Example 11), wherein the number of healthy cortical neurons is determined following 5-6 minutes of oxygen and glucose deprivation (OGD) in the presence or absence of those agents.
Figure 1E:
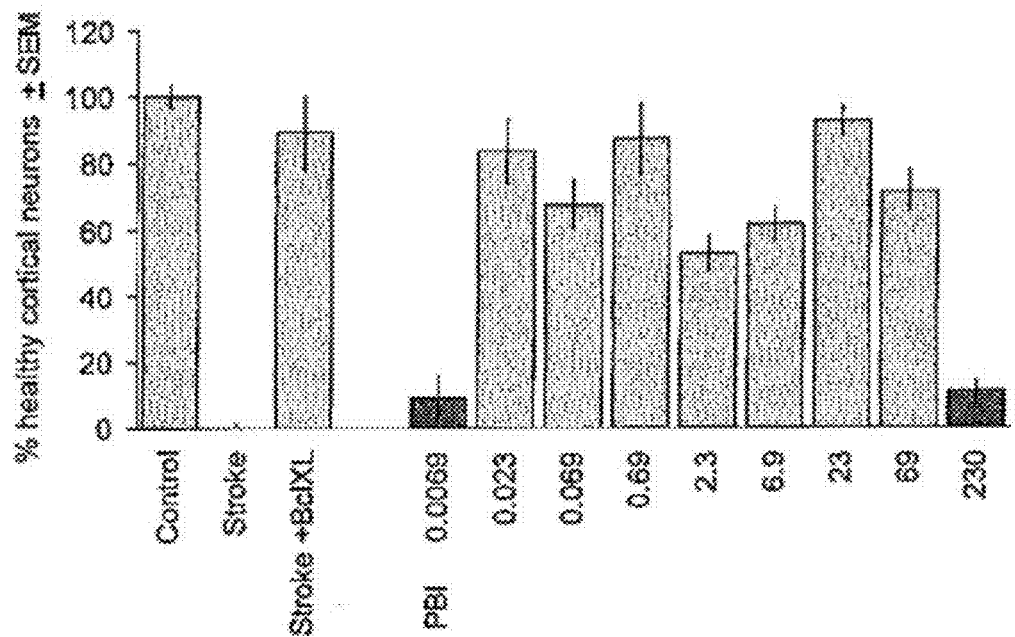
FIG. 1E depicts results of a concentration-response assay for an oleandrin-containing SCF extract in a neuroprotection brain-slice-based "stroke" assay as described herein (Example 11), wherein no oxygen or glucose deprivation is used as control.

Evidence of the existence of one or more pharmacologically active components, other than oleandrin, in the SCF extract was obtained by comparing the concentration-response curves for a solution containing pure oleandrin versus one containing the SCF extract. FIG. 1D depicts the results of a concentration-response assay for an aqueous solution containing pure oleandrin in a neuroprotection brain-slice-based "stroke" assay as described in Example 11. The concentration of oleandrin in the aqueous solution was varied from 0.0069 to 230 µg/ml. FIG. 1E depicts results of a concentration-response assay for an oleandrin-containing SCF *Nerium* species extract in a neuroprotection brain-slice-based "stroke" assay as described herein (Example 11). The data demonstrate that the extract is more efficacious than pure oleandrin meaning the extract contains one or more pharmacologically active agents that provide neuroprotection. Evidence of the identity of these other active agents was obtained by fractionation of the extraction and isolation of individual components thereof. The one or more pharmacologically active agents were determined to be oleanolic acid, ursolic acid and betulinic acid.

Example 11 provides a detailed description of an in vitro assay used to evaluate the efficacy of the extract, or composition thereof, for the treatment of stroke-mediated ischemic neuronal injury. The assay is a brain slice-based assay for oxygen and glucose deprivation (OGD) used to induce ≥50% loss of healthy cortical neurons by 24 hours. The parent unfractionated SCF extract of *Nerium* species, e.g. *Nerium oleander*, is used as a positive control.

Accordingly, the invention provides a method of protecting neurons against loss of activity caused by oxygen depletion or oxygen-glucose depletion by exposing the oxygen depleted and/or glucose-depleted neurons to an effective amount of oleandrin or oleandrin-containing extract to minimize loss of activity, reduce the rate of loss of activity, stop the loss of activity, slow down onset of loss of activity, and/or protect the function of neurons caused by exposing the oxygen depleted and/or glucose-depleted conditions.

Figure 3A:
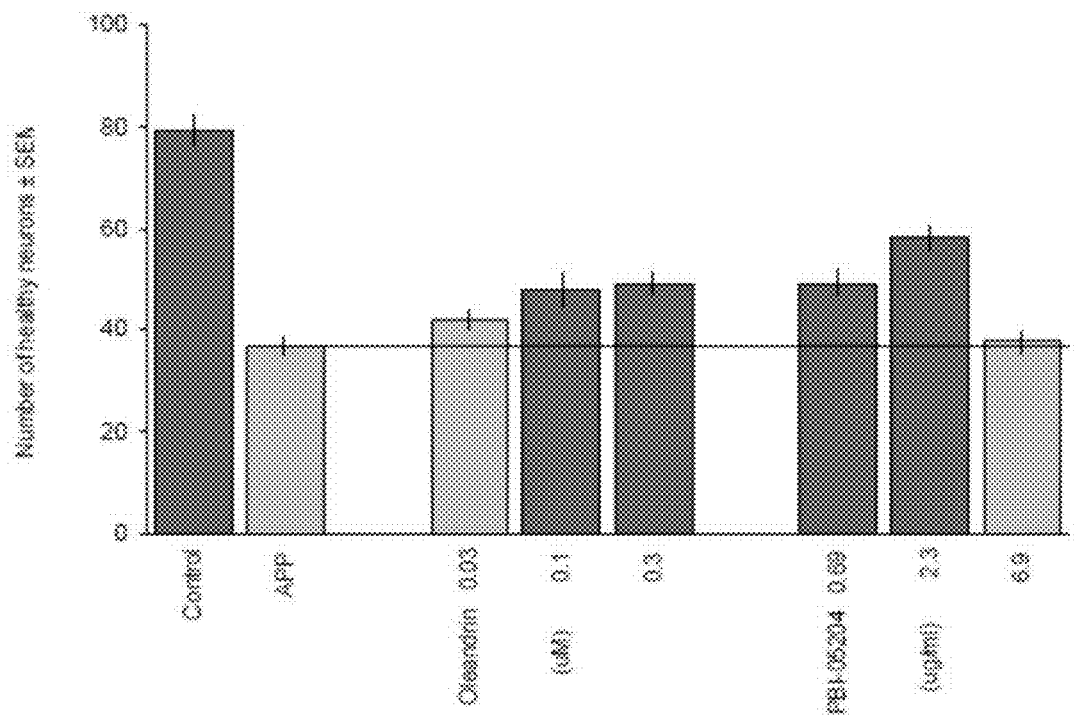
FIGS. 3A-3C depict results of the comparative evaluation of oleandrin versus oleandrin extract in a neuroprotection brain-slice-based "Alzheimer's" assay (Example 9), wherein the number of healthy cortical neurons is determined following APP/Aβ-induced degeneration in the absence or presence of varying amount of those agents.
Figure 3B:
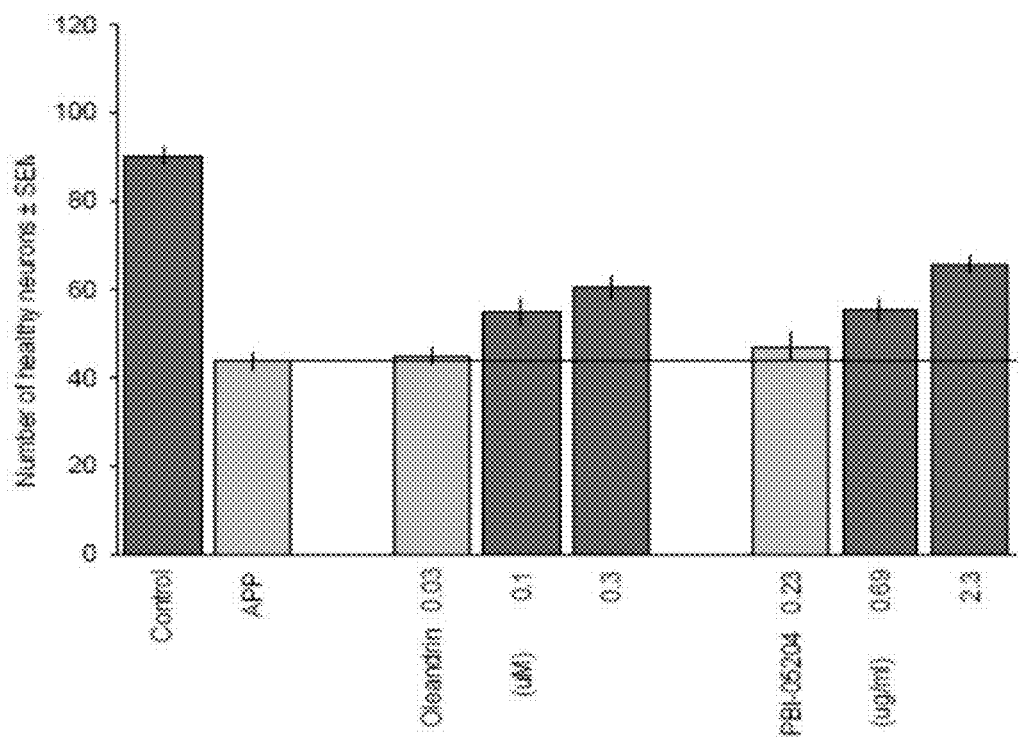
Figure 3C:
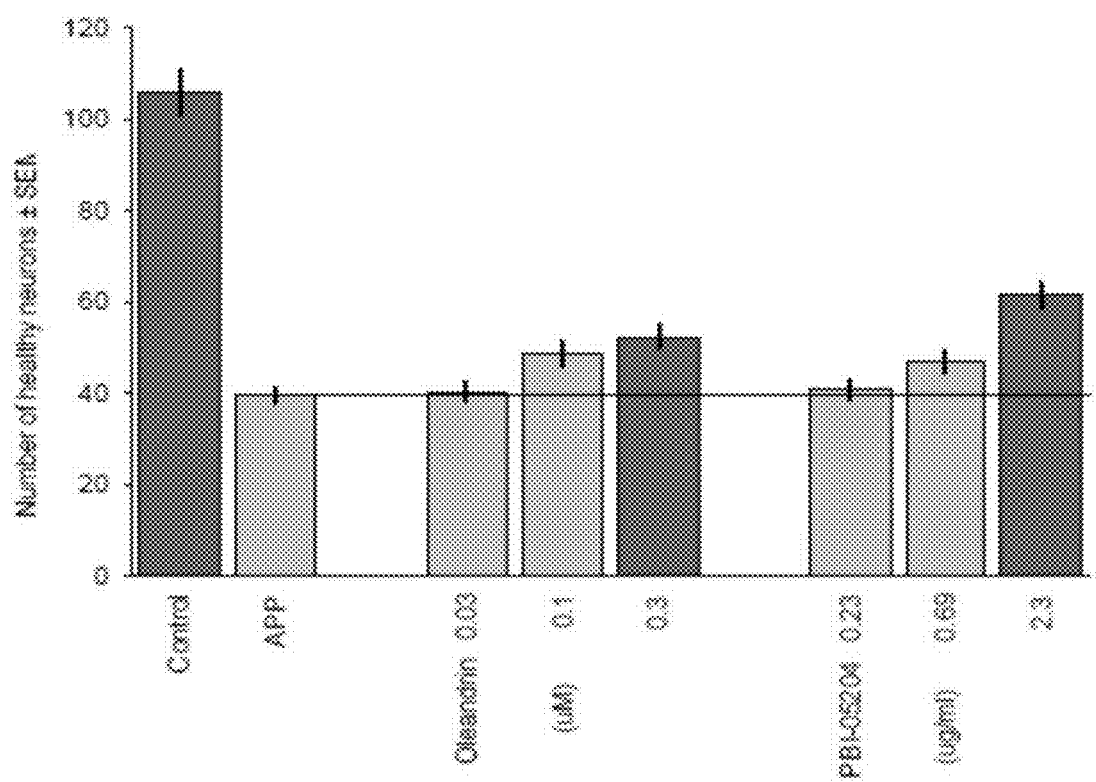

Example 9 provides a detailed description of an in vitro assay used to evaluate the efficacy of the cardiac glycosides for the treatment of Alzheimer's disease. The assay is a brain slice-based assay for APP/Aβ-induced (APP: amyloid precursor protein) degeneration of cortical pyramidal neurons. Upon cleavage by a secretase enzyme, the APP is reduced to Aβ peptides which are believed to be a causative factor in beta-amyloid plaque formation. Aβ proteins are associated with beta-amyloid plaque formation and are believed to be a hallmark if not etiologic factor in Alzheimer's disease. Biolistic transfection is used to introduce vital markers such as YFP (a marker yellow fluorescent protein) and to introduce disease gene constructs into the same neuronal populations in the brain slices. YFP is co-transfected with APP isoforms leading to the progressive degeneration of cortical pyramidal neurons over the course of three to four days after brain slice preparation and transfection. The data (FIGS. 3A-3C) indicate that oleandrin and an oleandrin-containing SCF extract provided a concentration-dependent neuroprotection to APP-transfected brain slices thereby rescuing levels nearly to the same levels as provided by BACE inhibitor drugs, i.e. beta secretase inhibitor drugs. The beta secretase enzyme cleaves the APP precursor protein into toxic Aβ-proteins. The oleandrin-containing SCF extract appeared to provide greater neuroprotection than oleandrin alone. The data in FIGS. 3A-3C are of significance in that few compounds or therapeutic strategies in the literature have shown any significant protection of neurons in this in vitro assay representative of Alzheimer disease. The data indicate that cardiac glycosides such as oleandrin will be effective as single agents, or in when present in extracts used as single therapy or combined with other products such as BASE inhibitors for the treatment of Alzheimer's disease.

Accordingly, the invention provides a method of protecting neurons against loss of activity caused by Alzheimer's disease, the method comprising: exposing the neurons exhibiting characteristics of Alzheimer's disease to an effective amount of oleandrin or oleandrin-containing extract to minimize loss of activity, reduce the rate of loss of activity, stop the loss of activity, slow down onset of loss of activity, and/or critical functioning of the neurons caused by Alzheimer's disease.

Example 10 provides a detailed description of an assay used to evaluate the efficacy of the cardiac glycosides for the treatment of Huntington's disease. Mutant htt protein is introduced via electroporation into high-density, mixed co-cultures of cortical neurons, striatal neurons, and glia. The striatal and cortical neurons are transfected with different color fluorescent proteins thereby facilitating the separate identification of the different types of neurons in the co-culture. The color fluorescent proteins are fluorescent and 'emit' color upon activation with a light source of appropriate wavelength. The data (FIGS. 4A-4D) indicate that oleandrin and oleandrin-containing SCF extract are more effective than KW6002 (an adenosine 2a receptor antagonist) in terms of providing a greater number of surviving neurons. Accordingly, the invention provides a method of protecting neurons against loss of activity caused by Huntington's disease, the method comprising: exposing the neurons exhibiting characteristics of Huntington's disease to an effective amount of oleandrin or oleandrin-containing extract to minimize loss of activity, reduce the rate of loss of activity, stop the loss of activity, slow down onset of loss of activity, and/or normal function of the neurons caused by Huntington's disease.

Figure 5:
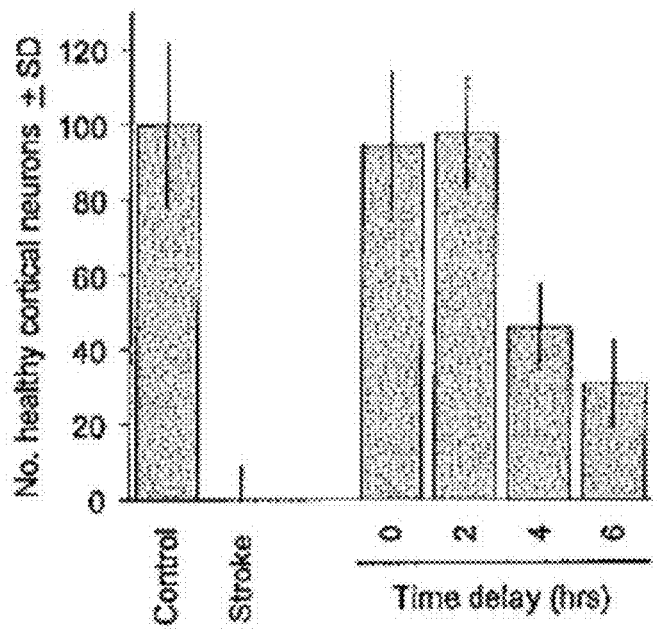
FIG. 5 depicts the results of a time-delayed neuroprotection brain-slice-based "stroke" assay as described herein (Example 13), wherein the "stroked" brain tissue is treated with cardiac glycoside-containing solution (oleandrin-containing SCF extract) after expiration of about 2, about 4 or about 6 hours following OGD.
Figure 6:
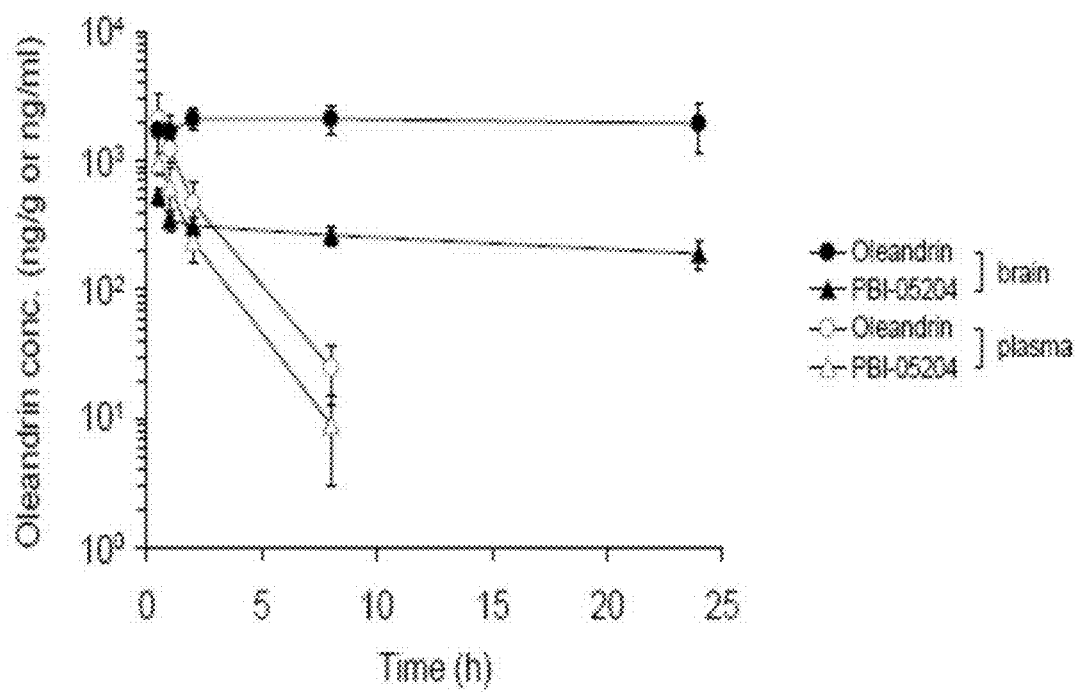
FIG. 6 depicts a plot of the concentration-time relation in plasma and brain tissue for oleandrin over a 24-hour period following i.p. administration of an oleandrin-containing SCF extract (triangles, identifier code: PBI-05204) and oleandrin (circles) in CD1 mice. Mean±SD oleandrin concentration in brain (ng/g) and plasma (ng/ml) for 5 mice are shown. PBI-05204 (38 mg/kg containing 0.8 mg/kg oleandrin, 50 µl) and oleandrin (3 mg/kg, 100 µl) were dissolved in DMSO:PEG400 vehicle, 50:50 v/v (PBI-05204, 28.6 mg/ml) or 25:75 v/v (oleandrin, 1 mg/ml). Control groups received DMSO:PEG400 vehicle alone. At 0.5, 1, 2, 4, 8 and 24 hours, plasma and brain tissue were harvested for LC/MS/MS analysis. Rapid and sustained CNS penetration was observed following both PBI-05204 and oleandrin administration.
Figure 7A:
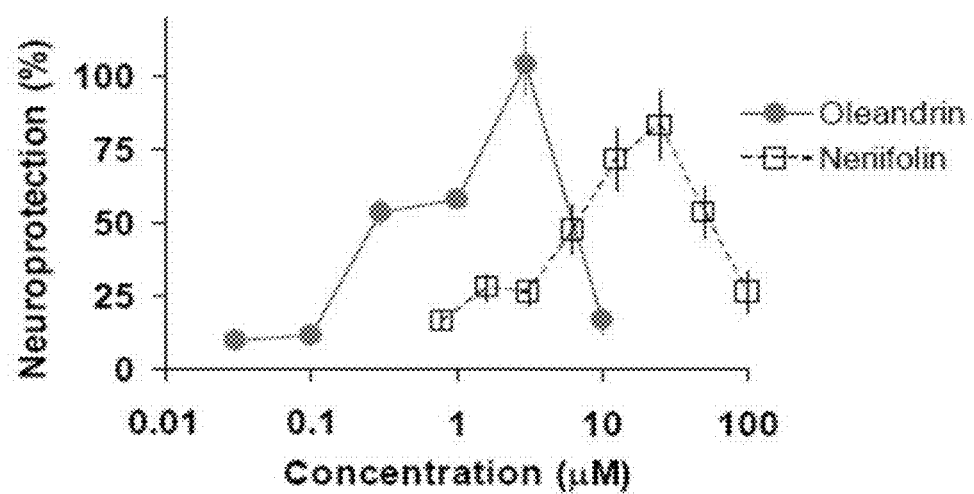
FIGS. 7A and 7B depict the results of a neuroprotection brain-slice based assay conducted as described herein.
Figure 7B:
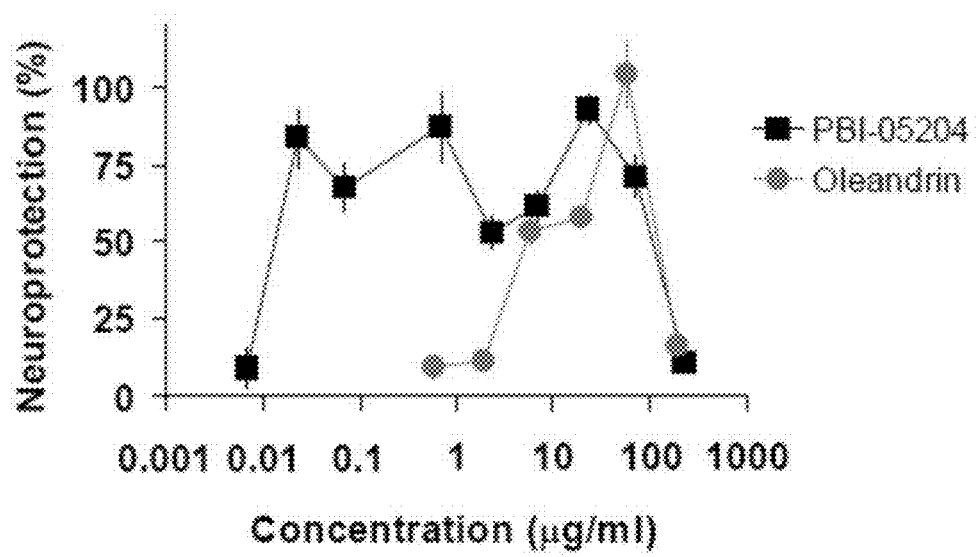

Example 13 details an exemplary brain-slice assay used as a model to evaluate the efficacy of cardiac glycoside in the treatment of stroke in a subject following completion of a delay period after the stroke. The brain-slice assay with oxygen glucose deprivation was conducted as described herein; however, rather than treating the brain slices prophylactically with cardiac glycoside, they were treated with the cardiac glycoside after delay periods of 0, 1, 2, 4, and 6 hours. The data, summarized in FIG. 5, demonstrates that cardiac glycoside, such as oleandrin or an SCF extract containing oleandrin, is effective at providing significant neuroprotection for delay periods of up to 1, up to 2, up to 3, up to 4, up to 5, up to about 6 hours after the stroke.

Accordingly, the invention provides a time-delayed method of treating stroke in a subject by administration of a dose of cardiac glycoside to a subject after the subject has suffered a stroke. Within an acceptable delay period (up to 1 hour, up to 2 hours, up to 3 hour, up to 4 hours, up to 5 hours, up to about 6 hours) after a subject has suffered the stroke, an initial dose of cardiac glycoside is administered according to an initial dosing regimen. Then, adequacy of the subject's clinical response and/or therapeutic response to treatment with cardiac glycoside is determined. If the subject's clinical response and/or therapeutic response is adequate, then treatment with cardiac glycoside is continued as needed until the desired clinical endpoint is achieved. Alternatively, if the subject's clinical response and/or therapeutic response are inadequate at the initial dose and initial dosing regimen, the dose is escalated or deescalated until the desired clinical response and/or therapeutic response in the subject is achieved. Dose escalation or de-escalation can be performed in conjunction with a change in the dosing regimen, such as a change in dosing frequency or overall period of dose administration.

Some of the brain slice assays herein are conducted under conditions wherein the brain tissue is treated with cardiac glycoside prior to OGD. Under those conditions, the data establishes the utility of cardiac glycosides at prophylactically providing neuroprotection against damage caused by stroke.

If a clinician intends to treat a subject having a neurological condition with a combination of a cardiac glycoside and one or more other therapeutic agents, and it is known that the particular neurological condition, which the subject has, is at least partially therapeutically responsive to treatment with said one or more other therapeutic agents, then the present method invention comprises: administering to the subject in need thereof a therapeutically relevant dose of cardiac glycoside and a therapeutically relevant dose of said one or more other therapeutic agents, wherein the cardiac glycoside is administered according to a first dosing regimen and the one or more other therapeutic agents is administered according to a second dosing regimen. In some embodiments, the first and second dosing regimens are the same. In some embodiments, the first and second dosing regimens are different.

If the neurological condition being treated is Alzheimer's disease, the one or more other therapeutic agents can be selected from the group consisting of BACE inhibitors or acetylcholinesterase inhibitors. In some embodiments, the one or more other therapeutic agents can be selected from the group consisting of Namenda™ (memantine HCl), Aricept™ (donepezil), Razadyne™ (galantamine), Exelon™ (rivastigmine), and Cognex™ (tacrine).

If the neurological condition being treated is Huntington's disease, the one or more other therapeutic agents can be selected from the group consisting of natural products, anticonvulsants, NMDA (n-methyl d-aspartate) receptor antagonists, and sodium channel blockers. Exemplary agents include Vitamin E, Baclofen (a derivative of CoQ10), Lamotrigine (an anticonvulsant), remacemide (an anesthetic which is a low affinity NMDA antagonist), and riluzole (Na channel blocker). The efficacy of each of these agents is considered to be low (Mestre T. et al, Chochrane Database Systematic Reviews Jul. 8, 2009; 8(3): CD006455) on its own; however, it is expected that administration of a dosage form containing oleandrin or oleandrin-containing extract to subjects receiving one or more of these other agents will provide a subject, having a neurological disorder, an improved clinical affect as compared to administration of these agents absent the oleandrin.

If the neurological condition being treated is stroke-mediated ischemic brain injury (ischemic stroke), then the therapeutic treatments disclosed in the literature (Gutierrez M. et al. "Cerebral protectiuon, brain repair, plasticity and cell therapy in ischemic stroke" *Cerebrovasc. Dis.* 2009; 27 Suppl 1:177-186), e.g. intravenous thrombolysis, can be employed in addition to the oleandrin or oleandrin extract-based method of the invention. In some embodiments, the one or more other therapeutic agents can be selected from the group consisting of drugs such as Alteplase (a thrombolytic agent).

The one or more other therapeutic agents can be administered at doses and according to dosing regimens that are clinician-recognized as being therapeutically effective or at doses that are clinician-recognized as being sub-therapeutically effective. The clinical benefit and/or therapeutic effect provided by administration of a combination of cardiac glycoside and one or more other therapeutic can be additive or synergistic, such level of benefit or effect being determined by comparison of administration of the combination to administration of the individual cardiac glycoside and one or more other therapeutic agents. The one or more other therapeutic agents can be administered at doses and according to dosing regimens as suggested or described by the Food and Drug Administration, World Health Organization, European Medicines Agency (E.M.E.A.), Therapeutic Goods Administration (TGA, Australia), Pan American Health Organization (PAHO), Medicines and Medical Devices Safety Authority (Medsafe, New Zealand) or the various Ministries of Health worldwide.

The cardiac glycoside can be any cardiac glycoside known to possess Na,K-ATPase binding activity and/or HIF-1α (hypoxic inducing factor alpha) binding activity. The cardiac glycoside is capable of crossing the blood-brain barrier and being retained in brain tissue for an extended period of time following administration. In this regard, the cardiac glycoside should be retained in the brain for at least 8 hours following administration of the cardiac glycoside due to tissue binding and a consequent low clearance rate. The preferred cardiac glycoside is oleandrin.

The cardiac glycoside can be present in pure form or as a mixture with one or more other compounds. The cardiac glycoside can be present as part of an extract. The extract can be prepared by supercritical fluid (SCF) carbon dioxide ($CO_2$) extraction or a chemically modified form of such an extract (e.g. an extract that includes ethanol or was made using SCF $CO_2$ and ethanol; Example 1). The extract can be obtained by extraction of plant material with an organic solvent, e.g. ethanol, methanol, propanol or other such solvents. The extract can be obtained from plant or animal material. The animal material can be the exudate of a toad (e.g. *Bufo bufo*). The plant material can be plant mass such as obtained from *Nerium* species, such as *Nerium oleander*, or of *Thevetia* species, such as *Thevetia neriifolia* or *Thevetia puruviana* (otherwise known as yellow oleander). The extraction process can be conducted on a dried powder of *Nerium oleander* leaves prepared according to a process described in a currently-pending U.S. provisional application Ser. No. 60/653,210 filed Feb. 15, 2005 in the name of Addington or U.S. application Ser. No. 11/340,016 filed Jan. 26, 2006 in the name of Addington, U.S. application Ser. No. 11/191,650 filed Jul. 28, 2006 (now U.S. Pat. No. 7,402,325 issued Jul. 22, 2008) in the name of Addington, or PCT International Patent Application No. PCT/US06/29061 filed Jul. 26, 2006, the entire disclosures of which are hereby incorporated by reference, or by a process described herein.

As used herein, the term "oleandrin" is taken to mean all known forms of oleandrin unless otherwise specified. Oleandrin can be present in racemic, optically pure or optically enriched form. *Nerium oleander* plant material can be obtained, for example, from commercial plant suppliers such as Aldridge Nursery, Atascosa, Tex.

Our work has shown that oleandrin has a good ability to cross the BBB and once in the brain tissues to reside there for a prolonged period of time. That is, the residence time of oleandrin in the brain is longer than that expected given the clearance of this molecule from plasma of experimental animals. As such, the relatively long residence time of oleandrin in the brain provides a distinct advantage of this lipid soluble cardiac glycoside compared to water soluble cardiac glycosides such as digoxin.

The extract can be obtained by modified (e.g. ethanol) or unmodified supercritical fluid extraction of a cardiac glycoside-containing plant mass. The supercritical fluid extract can comprise at least one other cardiac glycoside pharmacologically active agent and/or at least one other non-cardiac glycoside pharmacologically active agent that contributes to the therapeutic efficacy of the cardiac glycoside when the extract is administered to a subject. It can contribute additively or synergistically to the therapeutic efficacy of the cardiac glycoside. As used herein, the term "non-cardiac glycoside pharmacologically active agent" (or component) means a compound that is not a cardiac glycoside.

The neuroprotective composition can comprise (consist essentially of) at least one cardiac glycoside and at least one triterpene as the pharmacologically active agents. For example, embodiments of the neuroprotective composition can comprise (consist essentially of): a) oleandrin and oleanolic acid; b) oleandrin and ursolic acid; c) oleandrin and betulinic acid; d) oleandrin, oleanolic acid and ursolic acid; e) oleandrin, ursolic acid and betulinic acid; f) oleandrin, oleanolic acid and betulinic acid; or f) oleandrin, oleanolic acid, ursolic acid and betulinic acid. The molar amounts for the oleandrin and triterpenes can be as described herein.

The extract can be prepared by different processes. The extract can be prepared according to the process described in U.S. Pat. No. 5,135,745, which is a procedure for the preparation of the extract of the plant in water. The aqueous extract reportedly contains several polysaccharides with molecular weights varying from 2 KD to 30 KD, oleandrin and oleandrigenin, odoroside and neritaloside. The polysaccharides reportedly include acidic homopolygalacturonans or arabinogalaturonans. U.S. Pat. No. 5,869,060 to Selvaraj et al. discloses hot water extracts of *Nerium* species and methods of production thereof, e.g. Example 2. The resultant extract can then be lyophilized to produce a powder. U.S. Pat. No. 6,565,897 (U.S. Pregrant Publication No. 20020114852 and PCT International Publication No. WO 2000/016793 to Selvaraj et al.) discloses a hot-water extraction process for the preparation of a substantially sterile extract. Erdemoglu et al. (I Ethnopharmacol. (2003) November 89(1), 123-129) discloses results for the comparison of aqueous and ethanolic extracts of plants, including *Nerium oleander*, based upon their anti-nociceptive and anti-inflammatory activities. Organic solvent extracts of *Nerium oleander* are disclosed by Adome et al. (*Afr. Health Sci.* (2003) August 3(2), 77-86; ethanolic extract), el-Shazly et al. (*J. Egypt Soc. Parasitol.* (1996), August 26(2), 461-473; ethanolic extract), Begum et al. (*Phytochemistry* (1999) February 50(3), 435-438; methanolic extract), Zia et al. (*J. Ethnolpharmacol.* (1995) November 49(1), 33-39; methanolic extract), and Vlasenko et al. (*Farmatsiia.* (1972) September-October 21(5), 46-47; alcoholic extract). U.S. Pregrant Patent Application Publication No. 20040247660 to Singh et al. discloses the preparation of a protein stabilized liposomal formulation of oleandrin for use in the treatment of cancer. U.S. Pregrant Patent Application Publication No. 20050026849 to Singh et al. discloses a water soluble formulation of oleandrin containing a cyclodextrin. U.S. Pregrant Patent Application Publication No. 20040082521 to Singh et al. discloses the preparation of protein stabilized nanoparticle formulations of oleandrin from the hot-water extract.

However, the preferred extract used in a neuroprotective composition is the extract obtained by supercritical fluid (SCF) extraction of *Nerium* species or *Thevetia* species. The SCF extraction can be conducted in the presence of a modifier in the supercritical fluid, such as ethanol, to enhance extraction of the desired compound(s) from the plant mass. Modifiers generally possess volatility between that of the supercritical fluid and of the compound being extracted, and they must be miscible with the supercritical fluid. In some embodiments, the modifier is a liquid at ambient conditions. By way of example and without limitation, a modifier can be selected from the group consisting of ethanol, methanol, propanol, acetone, ethyl acetate, methylene chloride, etc. The preferred solvent for SCF extraction is supercritical carbon dioxide optionally comprising modifier(s).

The extract is a mixture of pharmacologically active compounds, such as oleandrin or other cardiac glycosides, oleaside, and other plant materials. Oleandrin extract from a supercritical fluid process contains by weight a theoretical range of 0.9% to 2.5% oleandrin. SCF extracts comprising varying amount of oleandrin have been obtained. In one embodiment, the SCF extract comprises about 2% by wt. of oleandrin.

The SCF extract can comprise a mixture of various components. Some of those components include oleandrin, oleaside A, oleandrigenin, neritaloside, odoroside (Wang X, Plomley J B, Newman R A and Cisneros A. LC/MS/MS analyses of an oleander extract for cancer treatment, *Analytical Chem.* 72: 3547-3552, 2000), and other unidentified components. The SCF extractable unidentified components of the SCF extract can include at least one other cardiac glycoside pharmacologically active component and/or at least one other non-cardiac glycoside pharmacologically active component that contributes to the efficacy of the oleandrin in the SCF extract. That is, at least one other SCF extractable component functions additively or synergistically with the oleandrin to provide the observed efficacy.

Figure 8:
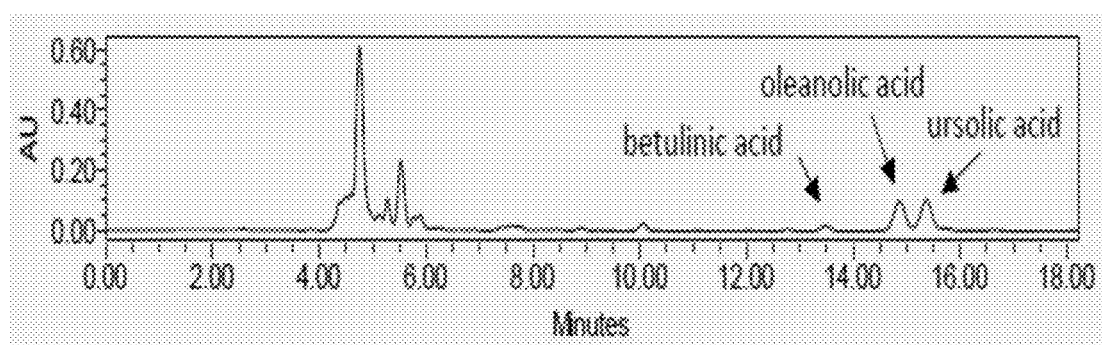
FIG. 8 depicts an HPLC chromatogram indicating the major components of PBI-05204), which is the SCF extract of *Nerium oleander* plant material. HPLC analysis was conducted according to Example 17, and the SCF extract was prepared as described herein. The triterpenes OA, UA and BA are eluted after other components, e.g. oleandrin, of the SCF extract.

The composition of the SCF extract PBI-05204 was determined according to Examples 14 and 17. An HPLC chromatogram of the SCF extract, obtained according to Example 17 is depicted in FIG. 8. The major neuroprotective pharmacologically active components of the SCF extract PBI-05204 include oleandrin, oleanolic acid, ursolic acid and betulinic acid. The approximate amount (weight: mg) of each component per gram of SCF extract is detailed in the table below. The exact amount of each component may vary due to manufacturing variability.

| Component | Approximate Amount (mg component per g of SCF extract) | Approximate Amount (mole of component per mole of oleandrin) |
|---|---|---|
| Oleandrin | 1-20 | 0.5-1.5 |
| Oleanolic acid | 60-80 | 4-6 |
| Ursolic acid | 60-80 | 4-6 |
| Betulinic acid | 0.1-20 | 0.1-1 |

Accordingly, a neuroprotective composition is made either by extraction or by mixing the individual components (oleandrin and triterpene(s)) according to the molar ratios described herein. Example 18 details a method for preparing a neuroprotective composition from the individual components.

It has been determined that an extract comprising oleandrin or oleandrin and one or more other pharmacologically active components (cardiac glycoside and/or non-cardiac glycoside) can provide neuroprotection. The primary pharmacologically active non-cardiac glycoside components of the SCF extract are triterpenes, e.g. oleanolic acid, ursolic acid and betulinic acid. Accordingly, the SCF extract of the invention comprises (or consists essentially of) oleandrin and one or more triterpenes (as set forth herein), which together provide improved neuroprotection as compared to the individual components thereof.

Further evidence of the existence of one or more biologically active components (triterpenes), other than oleandrin, in the SCF extract was obtained by comparing the concentration-response curves for an aqueous solution containing pure oleandrin versus one containing the SCF extract. FIG. 1D depicts the results of a concentration-response assay for an aqueous solution containing pure oleandrin in a neuroprotection brain-slice-based "stroke" assay as described in Example 11. The concentration of oleandrin in the aqueous solution was varied from 0.0069 to 230 µg/ml.

FIG. 1E depicts results of a concentration-response assay for an oleandrin-containing SCF extract in a neuroprotection brain-slice-based "stroke" assay as described herein. The data demonstrate that the SCF extract (or neuroprotective composition consisting essentially of (consisting primarily of) oleandrin, oleanolic acid, ursolic acid and betulinic acid) is more efficacious than pure oleandrin meaning the extract contains one or more pharmacologically active agents (triterpenes: oleanolic acid, ursolic acid, betulinic acid) that together provide neuroprotection which is improved over oleandrin alone.

It is possible that the extracts also differ in their relative performance as determined by efficacy in the assays included herein. Even so, if a cardiac glycoside is present in a sufficiently high amount or concentration in the extract to be able to prepare a therapeutically relevant dose thereof, then the extract is considered part of the invention. The triterpene(s) is(are) also present in sufficiently high amount or concentration in the extract to be able to prepare a therapeutically relevant dose thereof.

The neuroprotective composition can be formulated in any suitable pharmaceutically acceptable dosage form. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

The amount of neuroprotective composition incorporated in a dose of the invention will be at least one or more dosage forms and can be selected according to known principles of pharmacy. An effective amount or therapeutically relevant (effective) amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response may occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The desired dose for oral administration is up to 5 dosage forms although as few as one and as many as ten dosage forms may be administered. Exemplary dosage forms contain 0.6 mg, 0.01-100 mg or 0.01-100 microg of the SCF extract per dosage form, for a total 0.6 to 60 mg or 0.01-500 mg (1 to 10 dose levels) per dose.

The neuroprotective composition can be present in a dosage form in an amount sufficient to provide a subject with an initial dose of oleandrin of 12 microg to 300 microg or 12 microg to 120 microg, or more or less. A dosage form can comprise 0.01 microg to 100 mg or 0.01 microg to 100 microg of oleandrin, oleandrin extract or extract of *Nerium oleander* containing oleandrin.

of cardiac glycoside within a period of 0.5 to 1 hours or less. Some embodiments of the dosage form are enteric coated and release their charge of cardiac downstream of the stomach, such as from the jejunum, ileum, small intestine, and/or large intestine (colon). Enterically coated dosage forms will release cardiac glycosides into the systemic circulation within 1-10 hr after oral administration.

Based on preliminary animal dosing data it is anticipated that 50 to 75% of an administered dose of oleander extract will be orally bioavailable therefore providing 0.25 to 0.4 microg, 0.1 to 50 microg, 0.1 to 40 microg, 0.2 to 40 microg, 0.2 to 30 microg, 0.2 to 20 microg, 0.2 to 10 microg, 0.2 to 5 microg, 0.2 to 2.5 microg, 0.2 to 2 microg, 0.2 to 1.5 microg, 0.2 to 1 microg, 0.2 to 0.8 microg, 0.2 to 0.7, or 0.25 to 0.5 microg of oleandrin per dosage form. Given an average blood volume in adult humans of 5 liters, the anticipated oleandrin plasma concentration will be in the range of 0.05 to 2 ng/ml, 0.005 to 10 ng/mL, 0.005 to 8 ng/mL, 0.01 to 7 ng/mL, 0.02 to 7 ng/mL, 0.03 to 6 ng/mL, 0.04 to 5 ng/mL, or 0.05 to 2.5 ng/mL. The recommended daily dose of oleandrin, present in the SCF extract, is generally about 0.25 to about 50 microg twice daily or about 0.9 to 5 microg twice daily or about every 12 hours. The dose can be about 0.5 to about 100 microg/day, about 1 to about 80 microg/day, about 1.5 to about 60 microg/day, about 1.8 to about 60 microg/day, about 1.8 to about 40 microg/day. The maximum tolerated dose can be about 100 microg/day, about 80 microg/day, about 60 microg/day, about 40 microg/day, about 38.4 microg/day or about 30 microg/day of oleander extract containing oleandrin and the minimum effective dose can be about 0.5 microg/day, about 1 microg/day, about 1.5 microg/day, about 1.8 microg/day, about 2 microg/day, or about 5 microg/day.

It should be noted that a compound herein might possess one or more functions in the formulation of the invention. For example, a compound might serve as both a surfactant and a water miscible solvent or as both a surfactant and a water immiscible solvent.

A liquid composition can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, acetone, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or

| Composition | Oleandrin (moles) | Oleanolic acid (moles) | Ursolic acid (moles) | Betulinic acid (moles) | Suitable dose |
|---|---|---|---|---|---|
| A | 0.5-1.5 | 4-6 | — | — | 0.05 to 0.5 mg/kg/day |
| B | 0.5-1.5 | 4-6 | 4-6 | — | 0.05 to 0.35 mg/kg/day |
| C (PBI-05204) | 0.5-1.5 | 4-6 | 4-6 | 0.1-1 | 0.05 to 0.22 mg/kg/day |
| D | 0.5-1.5 | — | 4-6 | — | 0.05 to 0.4 mg/kg/day |
| E | 0.5-1.5 | — | — | 0.1-1 | 0.05 to 0.4 mg/kg/day |
| AA | About 1 | — | — | 0.3-0.7 | 0.05 to 0.4 mg/kg/day |
| AB | About 1 | About 4.7 | — | — | 0.05 to 0.5 mg/kg/day |
| AC | About 1 | About 4.7 | About 4.5 | — | 0.05 to 0.4 mg/kg/day |
| AD (PBI-05204) | About 1 | About 4.7 | About 4.5 | About 0.6 | 0.05 to 0.22 mg/kg/day |
| AE | About 1 | — | About 4.5 | — | 0.05 to 0.4 mg/kg/day |
| AF | About 1 | — | — | About 0.6 | 0.05 to 0.3 mg/kg/day |

All values are approximate, meaning "about" the specified value.

For use in treatment of mammals, the cardiac glycoside can be included in a dosage form. Some embodiments of the dosage form are not enteric coated and release their charge animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals. Exemplary solvents are listed as class 2 or class 3 solvents. Class 3 solvents include, for example, acetic acid, acetone, anisole, 1-butanol, 2-butanol, butyl acetate, tert-butlymethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

Other materials that can be used as water immiscible solvents in the invention include: Captex 100: Propylene Glycol Dicaprate; Captex 200: Propylene Glycol Dicaprylate/Dicaprate; Captex 200 P: Propylene Glycol Dicaprylate/Dicaprate; Propylene Glycol Dicaprylocaprate; Captex 300: Glyceryl Tricaprylate/Caprate; Captex 300 EP/NF: Glyceryl Tricaprylate/Caprate Medium Chain Triglycerides; Captex 350: Glyceryl Tricaprylate/Caprate/Laurate; Captex 355: Glyceryl Tricaprylate/Caprate; Captex 355 EP/NF: Glyceryl Tricaprylate/Caprate Medium Chain Triglycerides; Captex 500: Triacetin; Captex 500 P: Triacetin (Pharmaceutical Grade); Captex 800: Propylene Glycol Di (2-Ethythexanoate); Captex 810 D: Glyceryl Tricaprylate/Caprate/Linoleate; Captex 1000: Glyceryl Tricaprate; Captex CA: Medium Chain Triglycerides; Captex MCT-170: Medium Chain Triglycerides; Capmul GMO: Glyceryl Monooleate; Capmul GMO-50 EP/NF: Glyceryl Monooleate; Capmul MCM: Medium Chain Mono- & Diglycerides; Capmul MCM C8: Glyceryl Monocaprylate; Capmul MCM C10: Glyceryl Monocaprate; Capmul PG-8: Propylene Glycol Monocaprylate; Capmul PG-12: Propylene Glycol Monolaurate; Caprol 10G10O: Decaglycerol Decaoleate; Caprol 3GO: Triglycerol Monooleate; Caprol ET: Polyglycerol Ester of Mixed Fatty Acids; Caprol MPGO: Hexaglycerol Dioleate; Caprol PGE 860: Decaglycerol Mono-, Dioleate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent. A surfactant can be hydrophilic or hydrophobic.

The hydrophilic surfactant can be any hydrophilic surfactant suitable for use in pharmaceutical compositions. Such surfactants can be anionic, cationic, zwitterionic or nonionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

Examples of additional suitable solubilizer include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); amides, such as 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinypyrrolidone; esters, such as ethyl propionate, tributylcitrate,acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof; and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol nonoethyl ether (available from Gattefosse under the trade name Transcutol), and water. Mixtures of solubilizers are also within the scope of the invention.

Except as indicated, compounds mentioned herein are readily available from standard commercial sources.

The clear liquid composition is visually clear to the unaided eye, as it will contain less than 5%, less than 3% or less than 1% by wt. of suspended solids based upon the total weight of the composition.

Suitable dosage forms containing the neuroprotective composition can be prepared by mixing the neuroprotective composition with pharmaceutically acceptable excipients as described herein or as described in Pi et al. ("Ursolic acid nanocrystals for dissolution rate and bioavailability enhancement: influence of different particle size" in Curr. Drug Deliv. (March 2016), 13(8), 1358-1366), Yang et al. ("Self-microemulsifying drug delivery system for improved oral bioavailability of oleanolic acid: design and evaluation" in Int. J. Nanomed. (2013), 8(1), 2917-2926), Li et al. (Development and evaluation of optimized sucrose ester stabilized oleanolic acid nanosuspensions prepared by wet ball milling with design of experiments" in Biol. Pharm. Bull. (2014), 37(6), 926-937), Zhang et al. ("Enhancement of oral bioavailability of triterpene through lipid nanospheres: preparation, characterization, and absorption evaluation" in J. Pharm. Sci. (June 2014), 103(6), 1711-1719), Godugu et al. ("Approaches to improve the oral bioavailability and effects of novel anticancer drugs berberine and betulinic acid" in PLoS One (March 2014), 9(3):e89919), Zhao et al. ("Preparation and characterization of betulin nanoparticles for oral hypoglycemic drug by antisolvent precipitation" in Drug Deliv. (September 2014), 21(6), 467-479), Yang et al. ("Physicochemical properties and oral bioavailability of ursolic acid nanoparticles using supercritical anti-solvent (SAS) process" in Food Chem. (May 2012), 132(1), 319-325), Cao et al. ("Ethylene glycol-linked amino acid diester prodrugs of oleanolic acid for PEPT1-mediated transport: synthesis, intestinal permeability and pharmacokinetics" in Mol. Pharm. (August 2012), 9(8), 2127-2135), Li et al. ("Formulation, biological and pharmacokinetic studies of sucrose ester-stabilized nanosuspensions of oleanolic acid" in Pharm. Res. (August 2011), 28(8), 2020-2033), Tong et al. ("Spray freeze drying with polyvinylpyrrolidone and sodium caprate for improved dissolution and oral bioavailablity of oleanolic acid, a BCS Class IV compound" in Int. J. Pharm. (February 2011), 404(1-2), 148-158), Xi et al. (Formulation development and bioavailability evaluation of a self-nanoemulsified drug delivery system of oleanolic acid" in AAPS PharmSciTech (2009), 10(1), 172-182), Chen et al. ("Oleanolic acid nanosuspensions: preparation, invitro characterization and enhanced hepatoprotective effect" in J. Pharm. Pharmacol. (February 2005), 57(2), 259-264), the entire disclosures of which are hereby incorporated by reference.

Suitable dosage forms can also be made according to U.S. Pat. No. 8,187,644 B2 to Addington, which issued May 29, 2012, U.S. Pat. No. 7,402,325 B2 to Addington, which issued Jul. 22, 2008, U.S. Pat. No. 8,394,434 B2 to Addington et al, which issued Mar. 12, 2013, the entire disclosures of which are hereby incorporated by reference.

Although not necessary, a composition or kit of the present invention may include a chelating agent, preservative, antioxidant, adsorbents, acidifying agent, alkalizing agent, antifoaming agent, buffering agent, colorant, electrolyte, salt, stabilizer, tonicity modifier, diluent, other pharmaceutical excipient, or a combination thereof.

As used herein, the term "antioxidant" is intended to mean an agent that inhibits oxidation and is thus used to prevent the deterioration of preparations by the oxidative process. Such compounds include, by way of example and without limitation, ascorbic acid, ascorbic palmitate, Vitamin E, Vitamin E derivative, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

As used herein, the term chelating agent is intended to mean a compound that chelates metal ions in solution. Exemplary chelating agents include EDTA (tetrasodium ethylenediaminetetraacetate), DTPA (pentasodium diethylenetriamine-pentaacetate), HEDTA (trisodium salt of N-(hydroxyethyl)-ethylene-diaminetriacetic acid), NTA (trisodium nitrilotriacetate), disodium ethanoldiglycine ($Na_2EDG$), sodium diethanolglycine (DEGNa), citric acid, and other compounds known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide an alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium. Such compounds include, by way of example and without limitation, acetic acid, amino acid, citric acid, fumaric acid and other alpha-hydroxy acids, hydrochloric acid, ascorbic acid, and nitric acid and others known to those of ordinary skill in the art.

As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, FD&C Green No. 5, FD&C Orange No. 5, FD&C Red No. 8, caramel, and iron oxide (black, red, yellow), other FD&C dyes and natural coloring agents such as grape skin extract, beet red powder, beta-carotene, annato, carmine, turmeric, paprika, combinations thereof and other such materials known to those of ordinary skill in the art.

As used herein, the term "stabilizer" is intended to mean a compound used to stabilize an active agent against physical, chemical, or biochemical processes that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

The composition of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The composition can also include alcohol such as ethanol, isopropanol, hexadecyl alcohol, glycerol and propylene glycol; glycerol ketals such as 2,2-dimethyl-1,3-dioxolane-4-methanol; ethers such as poly (ethylene glycol) 450; petroleum hydrocarbons such as mineral oil and petrolatum; water; a pharmaceutically suitable surfactant, suspending agent or emulsifying agent; or mixtures thereof.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

One or more of the components of the formulation can be present in its free base or pharmaceutically or analytically acceptable salt form. As used herein, "pharmaceutically or analytically acceptable salt" refers to a compound that has been modified by reacting it with an acid as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences*, 17$^{th}$. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

A dosage form can be made by any conventional means known in the pharmaceutical industry. A liquid dosage form can be prepared by providing at least one liquid carrier and oleandrin or oleandrin-containing extract in a container. One or more other excipients can be included in the liquid dosage form. A solid dosage form can be prepared by providing at least one solid carrier and oleandrin or oleandrin-containing extract. One or more other excipients can be included in the solid dosage form.

A dosage form can be packaged using conventional packaging equipment and materials. It can be included in a pack, bottle, via, bag, syringe, envelope, packet, blister pack, box, ampoule, or other such container.

The invention includes a method for improving the clinical status of a statistically significant number of subjects of in a population of subjects having a neurological condition, the method comprising: administering to the population of subjects a cardiac glycoside or cardiac glycoside-containing composition; and determining the clinical status of the subjects. In some embodiments, the statistically significant number is at least 5%, at least 10%, at least 20%, at least 30%, at least 40%, at least 50%, at least 60%, at least 70%, at least 80% or at least 90% of the population. In some embodiments, the composition comprises oleandrin or an extract comprising oleandrin. The extract optionally comprises one or more other pharmacologically active compounds that cooperate with oleandrin to improve the clinical status of the subjects.

As used herein a "derivative" is: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. For example, a derivative may include a deuterated form, oxidized form, dehydrated, unsaturated, polymer conjugated or glycosilated form thereof or may include an ester, amide, lactone, homolog, ether, thioether, cyano, amino, alkylamino, sulfhydryl, heterocyclic, heterocyclic ring-fused, polymerized, pegylated, benzylidenyl, triazolyl, piperazinyl or deuterated form thereof.

As used herein, the individually named triterpenes can independently be selected upon each occurrence in their native (unmodified) form, in their salt form, in derivative form, prodrug form, or a combination thereof. Compositions containing and methods employing deuterated forms of the triterpenes are also within the scope of the invention.

Oleanolic acid derivatives, prodrugs and salts are disclosed in US 20150011627 A1 to Gribble et al. which published Jan. 8, 2015, US 20140343108 A1 to Rong et al which published Nov. 20, 2014, US 20140343064 A1 to Xu et al. which published Nov. 20, 2014, US 20140179928 A1 to Anderson et al. which published Jun. 26, 2014, US 20140100227 A1 to Bender et al. which published Apr. 10, 2014, US 20140088188 A1 to Jiang et al. which published Mar. 27, 2014, US 20140088163 A1 to Jiang et al. which published Mar. 27, 2014, US 20140066408 A1 to Jiang et al. which published Mar. 6, 2014, US 20130317007 A1 to Anderson et al. which published Nov. 28, 2013, US 20130303607 A1 to Gribble et al. which published Nov. 14, 2013, US 20120245374 to Anderson et al. which published Sep. 27, 2012, US 20120238767 A1 to Jiang et al. which published Sep. 20, 2012, US 20120237629 A1 to Shode et al. which published Sep. 20, 2012, US 20120214814 A1 to Anderson et al. which published Aug. 23, 2012, US 20120165279 A1 to Lee et al. which published Jun. 28, 2012, US 20110294752 A1 to Arntzen et al. which published Dec. 1, 2011, US 20110091398 A1 to Majeed et al. which published Apr. 21, 2011, US 20100189824 A1 to Arntzen et al. which published Jul. 29, 2010, US 20100048911 A1 to Jiang et al. which published Feb. 25, 2010, and US 20060073222 A1 to Arntzen et al. which published Apr. 6, 2006, the entire disclosures of which are hereby incorporated by reference.

Ursolic acid derivatives, prodrugs and salts are disclosed in US 20150011627 A1 to Gribble et al. which published Jan. 8, 2015, US 20130303607 A1 to Gribble et al. which published Nov. 14, 2013, US 20150218206 A1 to Yoon et al. which published Aug. 6, 2015, U.S. Pat. No. 6,824,811 to Fritsche et al. which issued Nov. 30, 2004, U.S. Pat. No. 7,718,635 to Ochiai et al. which issued May 8, 2010, U.S. Pat. No. 8,729,055 to Lin et al. which issued May 20, 2014, and U.S. Pat. No. 9,120,839 to Yoon et al. which issued Sep. 1, 2015, the entire disclosures of which are hereby incorporated by reference.

Betulinic acid derivatives, prodrugs and salts are disclosed in US 20150011627 A1 to Gribble et al. which published Jan. 8, 2015, US 20130303607 A1 to Gribble et al. which published Nov. 14, 2013, US 20120237629 A1 to Shode et al. which published Sep. 20, 2012, US 20170204133 A1 to Regueiro-Ren et al. which published Jul. 20, 2017, US 20170096446 A1 to Nitz et al. which published Apr. 6, 2017, US 20150337004 A1 to Parthasaradhi Reddy et al. which published Nov. 26, 2015, US 20150119373 A1 to Parthasaradhi Reddy et al. which published Apr. 30, 2015, US 20140296546 A1 to Yan et al. which published Oct. 2, 2014, US 20140243298 A1 to Swidorski et al. which published Aug. 28, 2014, US 20140221328 A1 to Parthasaradhi Reddy et al. which published Aug. 7, 2014, US 20140066416 A1 tp Leunis et al. which published Mar. 6, 2014, US 20130065868 A1 to Durst et al. which published Mar. 14, 2013, US 20130029954 A1 to Regueiro-Ren et al. which published Jan. 31, 2013, US 20120302530 A1 to Zhang et al. which published Nov. 29, 2012, US 20120214775 A1 to Power et al. which published Aug. 23, 2012, US 20120101149 A1 to Honda et al. which published Apr. 26, 2012, US 20110224182 to Bullock et al. which published Sep. 15, 2011, US 20110313191 A1 to Hemp et al. which published Dec. 22, 2011, US 20110224159 A1 to Pichette et al. which published Sep. 15, 2011, US 20110218204 to Parthasaradhi Reddy et al. which published Sep. 8, 2011, US 20090203661 A1 to Safe et al. which published Aug. 13, 2009, US 20090131714 A1 to Krasutsky et al. which published May 21, 2009, US 20090076290 to Krasutsky et al. which published Mar. 19, 2009, US 20090068257 A1 to Leunis et al. which published Mar. 12, 2009, US 20080293682 to Mukherjee et al. which published Nov. 27, 2008, US 20070072835 A1 to Pezzuto et al. which published Mar. 29, 2007, US 20060252733 A1 to Jansen et al. which published Nov. 9, 2006, and US 2006025274 A1 to O'Neill et al. which published Nov. 9, 2006, the entire disclosures of which are hereby incorporated by reference.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Oleandrin, oleanolic acid, ursolic acid and betulinic acid can be purchased from Sigma Chemical Co. (St. Louis, Mo.).

EXAMPLE 1

Supercritical Fluid Extraction of Powdered Oleander Leaves

Method A. With Carbon Dioxide.

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.94 kg.

The starting material was combined with pure $CO_2$ at a pressure of 300 bar (30 MPa, 4351 psi) and a temperature of 50° C. (122° F.) in an extractor device. A total of 197 kg of $CO_2$ was used, to give a solvent to raw material ratio of 50:1. The mixture of $CO_2$ and raw material was then passed through a separator device, which changed the pressure and temperature of the mixture and separated the extract from the carbon dioxide.

The extract (65 g) was obtained as a brownish, sticky, viscous material having a nice fragrance. The color was likely caused by chlorophyll. For an exact yield determination, the tubes and separator were rinsed out with acetone and the acetone was evaporated to give an addition 9 g of extract. The total extract amount was 74 g. Based on the weight of the starting material, the yield of the extract was 1.88%. The content of oleandrin in the extract was calculated using high pressure liquid chromatography and mass spectrometry to be 560.1 mg, or a yield of 0.76%.

Method B. With Mixture of Carbon Dioxide and Ethanol

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.85 kg.

The starting material was combined with pure $CO_2$ and 5% ethanol as a modifier at a pressure of 280 bar (28 MPa, 4061 psi) and a temperature of 50° C. (122° F.) in an extractor device. A total of 160 kg of $CO_2$ and 8 kg ethanol was used, to give a solvent to raw material ratio of 43.6 to 1. The mixture of $CO_2$, ethanol, and raw material was then passed through a separator device, which changed the pressure and temperature of the mixture and separated the extract from the carbon dioxide.

The extract (207 g) was obtained after the removal of ethanol as a dark green, sticky, viscous mass obviously containing some chlorophyll. Based on the weight of the starting material, the yield of the extract was 5.38%. The content of oleandrin in the extract was calculated using high pressure liquid chromatography and mass spectrometry to be 1.89 g, or a yield of 2.1%.

EXAMPLE 2

Hot-Water Extraction of Powdered Oleander Leaves

Hot water extraction is typically used to extract oleandrin and other active components from oleander leaves. Examples of hot water extraction processes can be found in U.S. Pat. Nos. 5,135,745 and 5,869,060.

A hot water extraction was carried out using 5 g of powdered oleander leaves. Ten volumes of boiling water (by weight of the oleander starting material) were added to the powdered oleander leaves and the mixture was stirred constantly for 6 hours. The mixture was then filtered and the leaf residue was collected and extracted again under the same conditions. The filtrates were combined and lyophilized. The appearance of the extract was brown. The dried extract material weighed about 1.44 g. 34.21 mg of the extract material was dissolved in water and subjected to oleandrin content analysis using high pressure liquid chromatography and mass spectrometry. The amount of oleandrin was determined to be 3.68 mg. The oleandrin yield, based on the amount of extract, was calculated to be 0.26%. The table below shows a comparison between the oleandrin yields for the two supercritical carbon dioxide extractions of Example 1 and the hot water extraction.

Comparison of Yields

| Extraction Medium | Oleandrin yield based on total extract weight |
|---|---|
| Supercritical Carbon Dioxide: Example 1, Method A | 0.76% |
| Supercritical Carbon Dioxide: Example 1, Method B | 2.1% |
| Hot Water Extraction: Example 2 | 0.26% |

EXAMPLE 3

Treatment of Neurological Condition Including but not Limited to Alzheimer's Disease Method A. Cardiac Glycoside Therapy A subject presenting with Alzheimer's disease is prescribed cardiac glycoside, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with cardiac glycoside is continued as needed and the dose or dosing regimen can be adjusted as needed until the patient reaches the desired clinical endpoint.

Method B. Combination Therapy: Cardiac Glycoside with Another Agent

Method A, above, is followed except that the subject is prescribed and administered one or more other therapeutic agents for the treatment of Alzheimer's disease, or symptoms thereof. Then one or more other therapeutic agents can be administered before, after or with the cardiac glycoside. Dose escalation (or de-escalation) of the one or more other therapeutic agents can also be done. Suitable one or more other therapeutic agents include Namenda™ (memantine HCl), Aricept™ (donepezil), Razadyne™ (galantamine), Exelon™ (rivastigmine), and Cognex™ (tacrine). An exemplary composition includes PBI-05204.

EXAMPLE 4

Treatment of Neurological Condition Including but not Limited to Huntington's Disease Method A. Cardiac Glycoside Therapy A subject presenting with Huntington's disease is prescribed cardiac glycoside, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with cardiac glycoside is continued as needed and the dose or dosing regimen can be adjusted as needed until the patient reaches the desired clinical endpoint. The doses administered can be similar to those of Example 3 or as otherwise described herein.

Method B. Combination Therapy: Cardiac Glycoside with Another Agent

Method A, above, is followed except that the subject is prescribed and administered one or more other therapeutic agents for the treatment of Huntington's disease, or symptoms thereof. The one or more other therapeutic agents can be administered before, after or with the cardiac glycoside. Dose escalation (or de-escalation) of the one or more other therapeutic agents can also be done. Suitable one or more other therapeutic agents include Vitamin E, Baclofen (a derivative of CoQ10), Lamotrigine (an anticonvulsant), remacemide (an anesthetic which is a low affinity NMDA antagonist), and riluzole (Na channel blocker). An exemplary composition includes PBI-05204.

EXAMPLE 5

Treatment of Neurological Condition Including but not Limited to Ischemic Stroke Method A. Cardiac Glycoside Therapy A subject presenting with ischemic stroke is prescribed cardiac glycoside, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with cardiac glycoside is continued as needed and the dose or dosing regimen can be adjusted as needed until the patient reaches the desired clinical endpoint. The doses administered can be similar to those in Example 3 or as otherwise described herein.

Method B. Combination Therapy: Cardiac Glycoside with Another Agent

Method A, above, is followed except that the subject is prescribed and administered one or more other therapeutic agents for the treatment of ischemic stroke, or symptoms thereof. The one or more other therapeutic agents can be administered before, after or with the cardiac glycoside. Dose escalation (or de-escalation) of the one or more other therapeutic agents can also be done. An exemplary composition includes PBI-05204.

EXAMPLE 6

HPLC Analysis of Solutions Containing Oleandrin

Samples (oleandrin standard, SCF extract and hot-water extract) were analyzed on HPLC (Waters) using the following conditions: Symmetry C18 column (5.0 μm, 150×4.6 mm I.D.; Waters); Mobile phase of MeOH:water=54:46 (v/v) and flow rate at 1.0 ml/min. Detection wavelength was set at 217 nm. The samples were prepared by dissolving the compound or extract in a fixed amount of HPLC solvent to achieve an approximate target concentration of oleandrin.

EXAMPLE 7

Determination of $\alpha 3$ and $\alpha 1$ Expression in Normal Neuronal Tissue

The procedures set forth in PCT International Application No. PCT/US08/82641, filed Nov. 6, 2008 in the name of Phoenix Biotechnology, Inc., the entire disclosure of which is hereby incorporated by reference, can be followed.

EXAMPLE 8

Evaluation of a Cardiac Glycoside in an In Vitro Assay for Stroke and Non-Stroke Method A. Stroke: Preparation of Cortical Brain Slices and OGD.

Neocortical brain slices were prepared from PND 7 Sprague-Dawley rat pups. The cerebral cortex was dissected, cut into 400-_m-thick slices and transferred into a container containing cold artificial cerebrospinal fluid with 1 uM MK-801 before plating; MK-801 was not included in any subsequent procedures. To mimic ischemic injury using transient oxygen-glucose deprivation (OGD), slices from one hemisphere of each brain were exposed to glucose-free, $N_2$-bubbled artificial cerebrospinal fluid for 7.5 min in a low $O_2$ (0.5%) environment. The OGD slices were then plated side-by-side with control slices from the contralateral hemisphere on nitrocellulose or Millicell (Millipore) permeable membranes, which were prepared identically except for no OGD. Thirty minutes after plating, the brain slice pairs were transfected, transferred to 24-well plates, and incubated at 37° C. under 5% $CO_2$ in humidified chambers. In each experiment, 5-6 minutes of oxygen-glucose deprivation (OGD) was used to induce >50% loss of healthy cortical neurons by 24 hrs (compare first two bars in FIG. 1A). A set concentration (3 µM) of neriifolin was used as the internal positive control. For oleandrin, all three concentrations from 0.3 to 3 µM appeared to provide neuroprotection in the first two experiments (FIGS. 1A and 1B), so the oleandrin concentrations tested were lowered in the third run (FIG. 1C) and suggested that the threshold concentration for neuroprotection lies between 0.1 and 0.3 µM.

Method B. Non-Stroke: Brain Slice Assay.

Figure 2A:
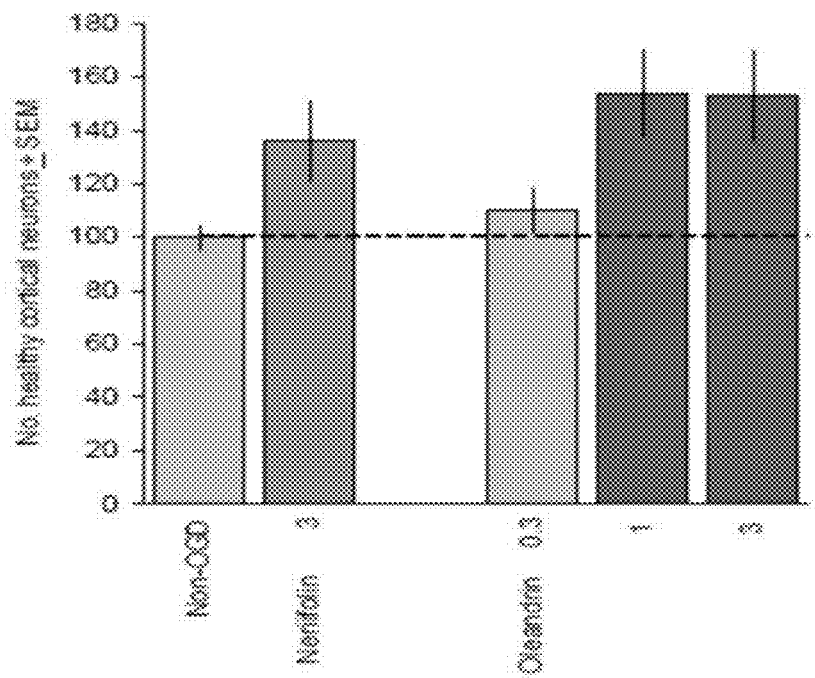
FIGS. 2A-2C depict results of the comparative evaluation of oleandrin versus neriifolin in a neuroprotection brain-slice-based "non-stroke" assay (Example 8), wherein the number of healthy cortical neurons is determined without OGD in the presence or absence of those agents.
Figure 2B:
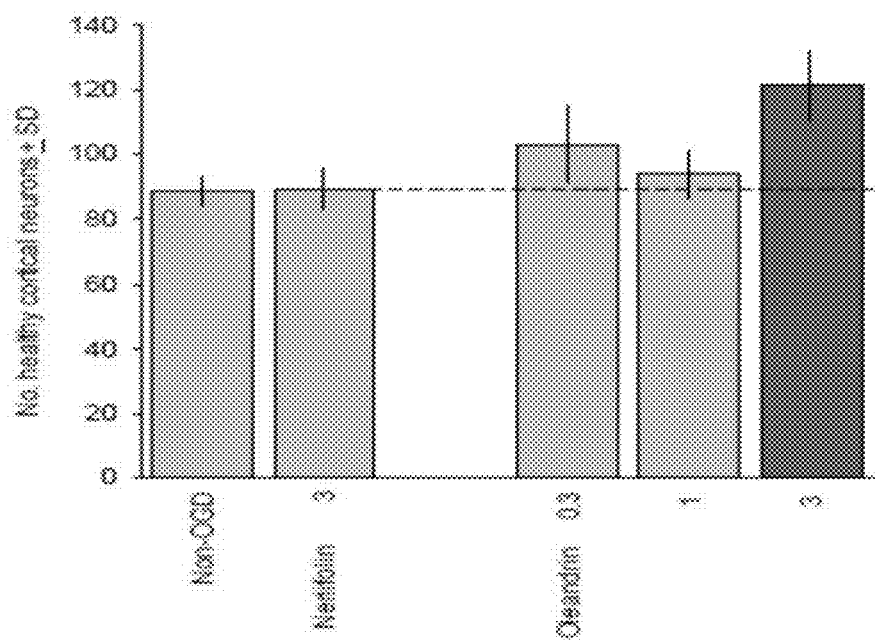
Figure 2C:
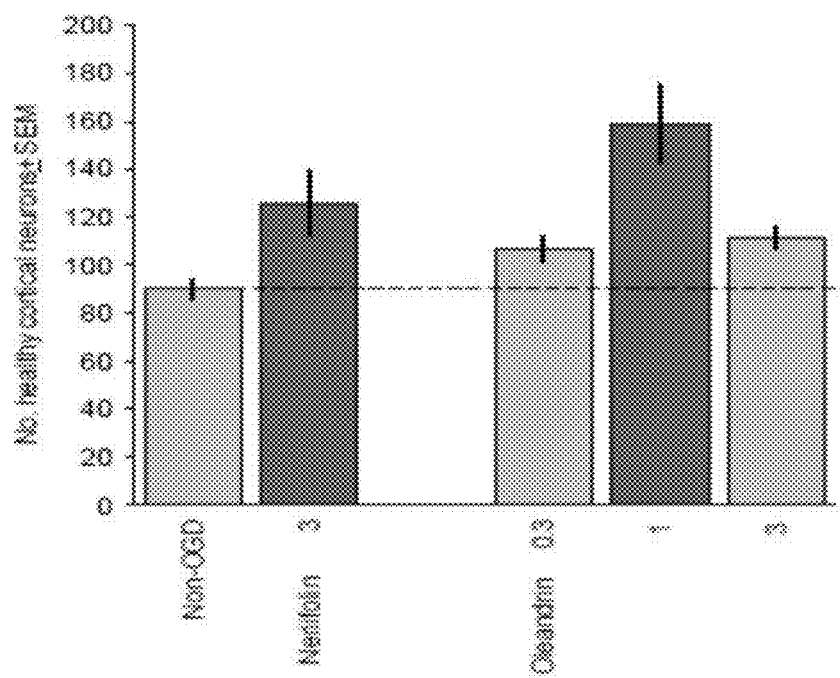

Oleandrin and PBI-05204 were tested on "nonstroked" brain slices; that is, ones that were sliced and transfected with YFP but not subjected to additional trauma via OGD. See experimental procedure outlined above. We have observed that a number of neuroprotective compounds, including neriifolin, can provide modest levels of neuroprotection to such brain slices, presumably by protecting against the trauma caused by the process of slicing and culturing itself. As can be seen in FIGS. 2A-2C oleandrin appeared to be able to provide neuroprotection to such "non-OGD" brain slices to similar levels as neriifolin signifying that cardiac glycosides mediate neuroprotection even in the absence of oxygen or glucose deprivation.

EXAMPLE 9

Evaluation of a Cardiac Glycoside in an In Vitro APP Assay for Alzheimer's Disease In the rat brain slice model for APP/Abeta-induced degeneration of cortical pyramidal neurons biolistic transfection is used not only to introduce vital markers such as YFP, but also to introduce disease gene constructs into the same neuronal populations in the brain slices. Thus, the APP/Aβ brain slice model co-transfects YFP with APP isoforms, leading to the progressive degeneration of cortical pyramidal neurons over the course of 3-4 days after brain slice preparation and transfection. As can be seen in the three runs in FIGS. 3A-3C, both oleandrin and PBI-05204 appeared able to provide dose-dependent neuroprotection to APP-transfected brain slices, rescuing to levels nearly to those that can be provided by BACE inhibitor drugs.

EXAMPLE 10

Evaluation of a Cardiac Glycoside in an In Vitro Corticostriatal Co-Culture Assay for Huntington's Disease In this assay, instead of using intact brain slices, mutant htt is introduced via electroporation into high-density, mixed co-cultures of cortical neurons, striatal neurons, and glia arrayed in 96-well plates. The goal of this assay platform is to combine the biological/clinical relevance of a complex primary culture system that recapitulates key aspects of the interconnectivity of disease-relevant neuronal populations in vivo, with the ability to conduct large-scale fully automated screening campaigns. In this assay, over the course of 1-2 weeks in vitro, transfected mutant htt constructs induce the progressive degeneration of both striatal and cortical neurons that are subsequently quantified using automated image acquisition and object detection algorithms on the Cellomics Arrayscan VTI platform. Each data point was drawn from 6 wells with 16 images in each well automatically captured, processed, and analyzed on the Cellomics Arrayscan using protocols developed during a large-scale screening campaign being conducted in association with the Cure Huntington's Disease Initiative. In a full run, some 25,000 images are collected and analyzed in each cycle, 4 cycles per week.

Cortico-Striatal Co-Culture Assay Platform.

Pure glial cultures are prepared in advance of neuronal plating to establish 96-well plates with confluent glial beds. Cortical and striatal tissue are then dissociated separately and "nucleofected" with appropriate DNA constructs and are distinguishable later by the expression of different fluorescent proteins such as YFP, CFP, and mCherry. These separately transfected cortical and striatal neurons are then mixed thoroughly and plated into the 96-well plates containing the previously plated glial monolayers.

Figure 4A:
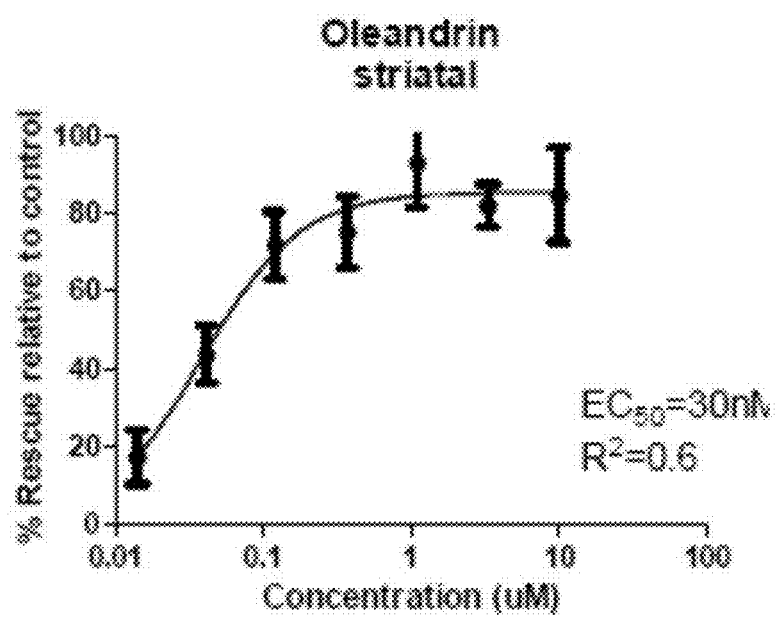
FIGS. 4A-4D depict results from duplicate experiments of the comparative evaluation of oleandrin in a neuroprotection cortico-striatal co-culture neuron-based "Huntington's disease" assay (Example 10), wherein the percent rescue, relative to control, of cortical neurons and striatal neurons transfected with a mutant form of the Huntington (htt) protein is determined in the absence or presence of varying amount of oleandrin.
Figure 4B:
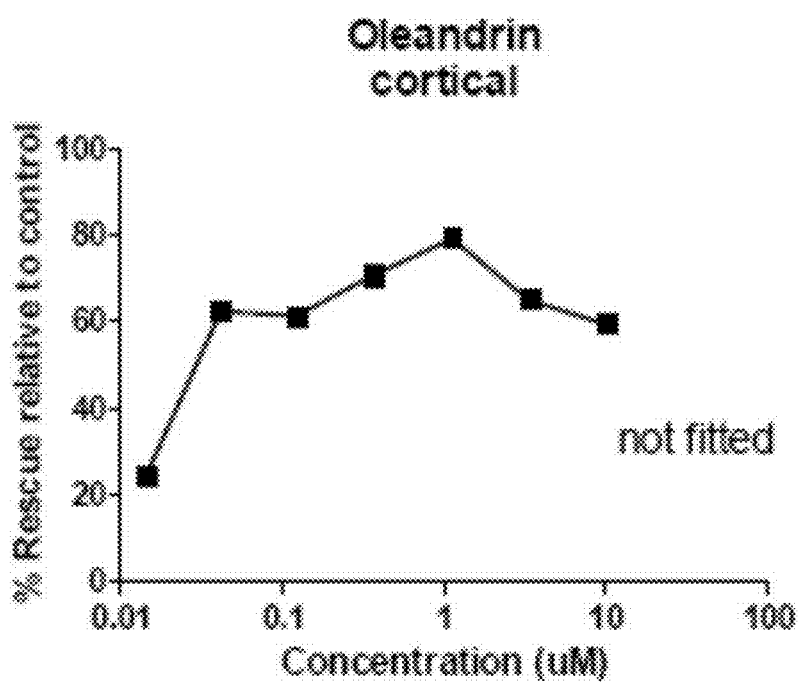
Figure 4C:
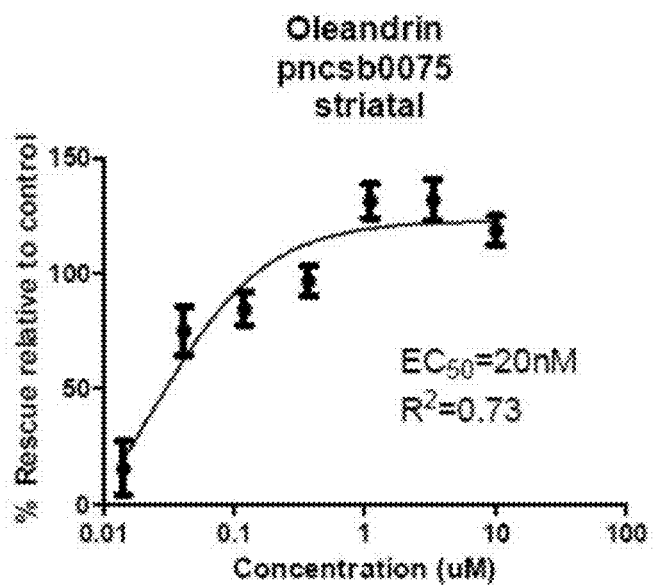
Figure 4D:
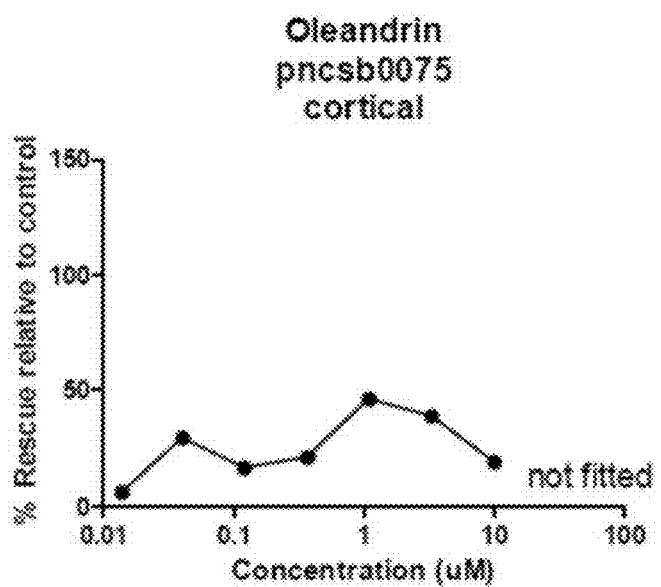
Figure 4E:
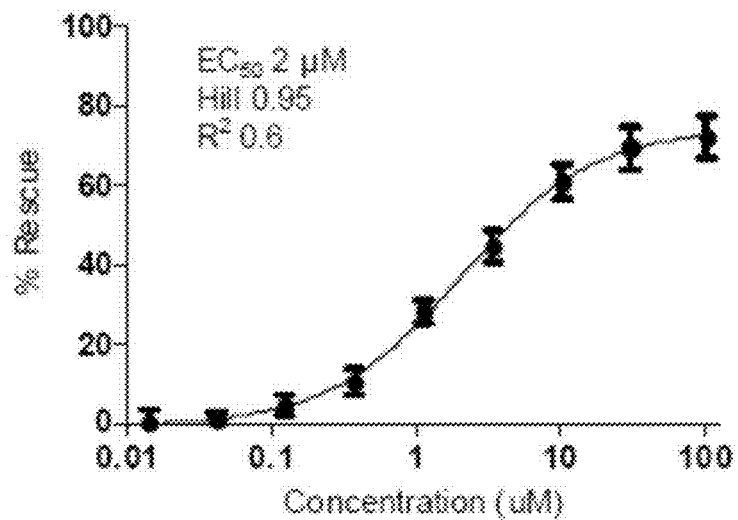
FIG. 4E depicts the concentration-response curve for oleandrin in terms of its relative ability to rescue neuronal injury and death due to transfection of Huntington's disease (results from in vitro assay; Example 10).

Both oleandrin and PBI-05204 (the supercritical $CO_2$ extract of *Nerium oleander*) were tested in this corticostriatal co-culture platform and preliminarily these compounds appear to be the strongest hits we have observed to date out of >400 late-stage drug molecules that have been evaluated in this assay system. For comparison, a dose-response graph for KW6002 (an adenosine 2a receptor antagonist), the compound that we routinely include as the positive control for this co-culture assay is included (see FIG. 4E). Efficacy of oleandrin is on par with KW6002, while its potency appears to be some 100-fold greater.

EXAMPLE 11

Evaluation of a Cardiac Glycoside and an Extract of the Invention in an In Vitro Assay for Stroke and Non-Stroke Method A. Stroke: Preparation of Cortical Brain Slices and OGD.

Neocortical brain slices were prepared from PND 7 Sprague-Dawley rat pups. The cerebral cortex was dissected, cut into 400-µ-thick slices and transferred into a container containing cold artificial cerebrospinal fluid with 1 uM MK-801 before plating; MK-801 was not included in any subsequent procedures. To mimic ischemic injury using transient oxygen-glucose deprivation (OGD), slices from one hemisphere of each brain were exposed to glucose-free, $N_2$-bubbled artificial cerebrospinal fluid for 7.5 min in a low $O_2$ (0.5%) environment. The OGD slices were then plated side-by-side with control slices from the contralateral hemisphere on nitrocellulose or Millicell (Millipore) permeable membranes, which were prepared identically except for no OGD. Thirty minutes after plating, the brain slice pairs were transfected, transferred to 24-well plates, and incubated at 37° C. under 5% $CO_2$ in humidified chambers. In each experiment, 5-6 minutes of oxygen-glucose deprivation (OGD) was used to induce >50% loss of healthy cortical neurons by 24 hrs. A set concentration (3 μM) of neriifolin (a cardiac glycoside) was used as the internal positive control. For oleandrin (a cardiac glycoside), all three concentrations from 0.3 to 3 μM appeared to provide neuroprotection in the first two experiments, so the oleandrin concentrations tested were lowered in the third run and suggested that the threshold concentration for neuroprotection lies between 0.1 and 0.3 μM. The unfractionated extract, e.g. of Nerium species, or a fraction thereof can also be used as described for the oleandrin.

Method B. Non-Stroke: Brain Slice Assay.

Oleandrin and PBI-05204, an unfractionated SCF extract of Nerium oleander, were tested on "nonstroked" brain slices; that is, ones that were sliced and transfected with YFP but not subjected to additional trauma via OGD. See experimental procedure outlined above. We have observed that a number of neuroprotective compounds, including neriifolin, can provide modest levels of neuroprotection to such brain slices, presumably by protecting against the trauma caused by the process of slicing and culturing itself. The data demonstrate that oleandrin and the extract appeared to be able to provide neuroprotection to such "non-OGD" brain slices to similar levels as neriifolin signifying that cardiac glycosides mediate neuroprotection even in the absence of oxygen or glucose deprivation.

EXAMPLE 12

HPLC Analysis of SCF Extract

The purpose of this assay is to identify extract containing cardiac glycoside. A sample from each extract was analyzed as follows. The extract (1-3 mg) was dissolved in 1-5 ml of aqueous methanol (80% methanol in water). The diluted sample (10-25 μl) was analyzed with an Agilent Zorbax SB-C18 column using 80% methanol in water as the mobile phase, a flow rate of 0.7 mL/min and DAD-UV effluent monitoring at the following wavelengths: 203, 210, 217, 230, 254, 280, 310 and 300 nm. Positive identification is confirmed via peak formation on a chromatogram when comparing retention times and spectra of extract samples to reference samples.

EXAMPLE 13

Time-Delay Brain-Slice Assay for Determination of Neuroprotection

This assay was conducted according to Example 11 except that the following changes were made. A specified length of time was allowed between OGD and introduction of a proposed neuroprotective agent. The ability of PBI-05204 to provide neuroprotection to brain slices if treatment was delayed relative to the timing of the OGD treatment was determined. Data showed that a 2 hr delay of Nerium oleander extracts was well tolerated, showing similar levels of neuroprotection to those attained with application of PBI-05204 immediately following OGD treatment. Neuroprotective benefit was reduced with 4 to 6 hr of delay of administration of PBI-05204, but at levels of neuroprotection that were still significantly and physiologically relevant.

EXAMPLE 14

Identification of Compounds in Nerium oleander SCF Extract Obtained According to Example 1 (Method B) in Unfractionated Form The SCF extract was analyzed by MS-DART TOF analysis as follows. A JEOL AccuTOF-DART mass spectrometer (Jeol U.S.A., Peobody, Mass., U.S.A.) was used.

A JEOL AccuTOF-DART mass spectrometer (Jeol USA, Peabody, Mass., USA) was used. Analyses were conducted in a positive ion mode (DART+) giving masses corresponding to the M+H+ ions generated by the DART-MS. A range of settings on the instrument was used to determine optimal conditions for N. oleander analyses. The general settings for DART+ included: needle voltage 3500 V; orifice 1-2-20 V; ring lens 2-5 V; orifice 2-2-5 V; and peaks voltage 1000 V. Calibrations were performed internally with each sample using a 10% solution of PEG 600 which provides mass markers throughout the required mass range of 100-1000 mass units. Other analyses were undertaken in the DART-mode and these consisted of: needle voltage 3500 V; heating element 250° C.; electrode 1—150 V; electrode 2—250 V; He gas flow rate 3.79 LPM. Mass spectrometer settings: MCP 2600 V; orifice 1—15 V; ring lens—5 V, orifice 2—5 V; and peaks voltage 1000 V. Calibrations were performed internally with each sample using a perfluorinated carboxylic acid solution that provides markers throughout the required mass range of 100-1000 mass units. The N. oleander samples were introduced neat into the DART helium plasma using the closed end of a borosilicate glass melting point tube. The capillary tube was held in the He plasma for approximately 3-5 s per analysis. Molecular formulas were confirmed by elemental composition and isotope matching programs provided with the JEOL AccuTOF DART-MS instrument. A searchable database of N. oleander constituents, developed by HerbalScience (Naples, Fla., USA) was used.

An exemplary batch of the SCF extract was found to contain at least the following components present in the indicated relative abundances (%).

| Component | Relative Abundance (%) |
|---|---|
| Oleandrin | 2.99 |
| Oleandrigenin | 3.31 |
| Ursolic acid/betulinic acid | 15.29 |
| Odoroside | 0.80 |
| Oleanolic acid | 0.60 |
| Urs-12-ene-3β,28-diol/betulin | 5.44 |
| 3β,3β-hydroxy-12-olean-en-28-oic acid | 14.26 |
| 28-norurs-12-en-36β-ol | 4.94 |
| Urs-12-en-3β-ol | 4.76 |

Batch-to-batch variability in relative content of the individual components was observed. The primary pharmacologically active components of the SCF extract are oleandrin, oleanolic acid, ursolic acid and betulinic acid. The relative amounts of these four components are set forth below.

| Component | Amount (mg component per g of SCF extract) | Amount (mole of component per mole of oleandrin) |
|---|---|---|
| Oleandrin | 1-40 | 0.5-1.5 |
| Oleanolic acid | 60-80 | 4-6 |
| Ursolic acid | 60-80 | 4-6 |
| Betulinic acid | 0.1-20 | 0.1-1 |

EXAMPLE 15

Evaluation of Neuroprotective Composition in Brain Slice-Based OGD Assay

The neuroprotective composition evaluated in this example is the SCF extract or a mixture of oleandrin and triterpene(s).

Coronal brain slices (250 μm thick) were prepared from postnatal day 10 Sprague-Dawley rat pups of either gender (Charles River) and established in organotypic culture. Animals were sacrificed in accordance with NIH guidelines and under Duke IACUC approval and oversight. Briefly, brain tissue slices were cut in ice-cold artificial cerebrospinal fluid (ACSF) and plated in interface configuration on top of culture medium (Neurobasal A medium supplemented with 15% heat-inactivated horse serum, 10 mM KCl, 10 mM HEPES, 100 U/ml penicillin/streptomycin, 1 mM sodium pyruvate, and 1 mM L-glutamine) set in 0.5% reagent-grade agarose. To model ischemic injury, brain slices were subjected to oxygen-glucose deprivation (OGD) by exposure to glucose-free, $N_2$-bubbled ACSF containing low $O_2$ (<0.5%) for 5.5 min.

One hour later, control and OGD-treated brain slices were biolistically transfected with DNAs encoding yellow fluorescent protein (YFP). For assays modeling neurodegeneration in AD or FTD, brain slices were co-transfected with YFP together with an expression construct to WT amyloid precursor protein (APP), or with YFP together with a cDNA constructed in house encoded human Tau4R0N (identical to NCBI Reference Sequence NM_016834), respectively. Brain slice explants were then incubated for 24 h under 5% $CO_2$ at 37° C. for OGD assays; or for 3 d for APP- and tau4R0N-induced neurodegeneration assays. Neuroprotective composition was added to culture medium at the time of brain slice explantation at the indicated concentrations.

For all brain slice assays, numbers of healthy pyramidal neurons in the cortical regions of each brain slice were imaged on a Leica MZIIIFL fluorescence stereomicroscope. Cortical pyramidal neurons were readily identified by their characteristic positions and orientations in the cortical plate, and by their prominent extension of a single, apical dendrite radially towards the pial surface. Healthy cortical pyramidal neurons were deemed as those 1) presenting a stout and brightly labeled cell body located within the pyramidal neuronal layers of the cortex; 2) retaining a clear apical dendrite extending radially towards the pial surface the slice; 3) expressing ≥2 clear basal dendrites ≥2 cell body diameters long directly from the neuronal soma; and 4) showing clear and continuous cytoplasmic labeling with the YFP visual marker in the soma and throughout all neuronal processes. Statistically significant differences with respect to the negative control condition (OGD, APP-transfected, or tau4R-transfected treated with DMSO carrier only) were determined using ANOVA followed by Dunnett's post hoc comparison test at the 0.05 confidence level, with N=12 brain slices per condition. Each experiment was carried out at least 3 times.

EXAMPLE 16

Evaluation of Neuroprotective Composition in Nrf2 Activation and ARE Gene Expression Nrf2 Activation The neuroprotective composition evaluated in this example is the SCF extract or a mixture of oleandrin and triterpene(s).

Primary corticostriatal neuronal co-cultures were prepared from E18 Sprague-Dawley rat or C57Bl/6 mouse embryos of either gender. For luciferase reporter assays, the Cignal Antioxidant Response Reporter kit (Qiagen) was used. The 5×ARE luciferase reporter mixture at 40:1 luciferase:Renilla plasmid was transfected into cortical and striatal neurons separately using an Amaxa electroporation device (Lonza). After electroporation, neurons were pooled and immediately plated into 96-well plates containing mature glial cultures. After culturing for 96 h, compounds were added at the indicated concentrations for 7 or 24 h prior to harvesting using Dual-Glo Luciferase Assay System protocol and reagents (Promega). Dual-wavelength luminescence was detected using a SpectraMax L microplate reader (Molecular Devices). Luciferase values were normalized to the internal Renilla control and fold-expression over the DMSO-only treatment control was calculated. At least 3 independent experiments were done using 4-6 biological replicates.

ARE Gene Expression

For qPCR quantification of ARE target gene expression levels, cortical and striatal neurons were plated onto 96-well plates containing mature glial cultures and cultured for 96 h. Neuroprotective composition was added to cultures at the indicated concentrations for 6 h. At the end of the treatment period, cells were lysed and total RNA was isolated using Absolutely RNA mini-prep kits (Agilent Technologies/Stratagene). cDNA was generated using oligo dT primers and Superscript II reverse transcriptase (Invitrogen). Resulting cDNA was used for quantitative PCR of gene transcripts using SYBR Green Real-Time PCR Master Mix (Life Technologies) and the following mouse primers, for: Gclc (forward-5' TGGCCACTATCTGCCCAATT-3' and reverse-5'-GTCTGACACGTAGCCTCGGTAA-3'), Nqo1 (forward-5'-GCCCGCATGCAGATCCT-3' and reverse 5'-GGTCTC-CTCCCAGACGGTTT3'), Srx (forward-5'-GCTTC-CTCTCGGGAGTCCTT-3' and reverse-5'-CAGCAACAGCGACTACGAAGTAA-3'), and Hmox1 (forward-5'-CCTCACTGGCAGGAAATCATC-3' and reverse-5'-CCTCGTGGAGACGCTTTACATA-3') (Integrated DNA Technologies). For rat corticostriatal co-culture samples, qPCR primers used were as previously described (van Roon-Mom, W. M. et al. Mutant huntingtin activates Nrf2-responsive genes and impairs dopamine synthesis in a PC12 model of Huntington's disease. BMC Molecular Biology (2008), 9, 1-13, doi:10.1186/1471-2199-9-84). Each biological sample was measured in triplicate on a ViiA 7 real-time PCR instrument (Applied Biosystems); fold expression was calculated after normalization to corresponding control GAPDH levels.

EXAMPLE 17

HPLC Analysis of Triterpene Components

PBI-05204 (the SCF extract) was prepared as described herein. The triterpene components thereof were quantified by HPLC using a Gemini C18 diphenyl column and eluting the triterpenes with an isocratic mobile phase consisting of 95% MeCN with 0.1% formic acid at a flow rate of 0.6 ml/min and a detection wavelength of 220 nm. Standard curves were developed and used to calculate the relative molar ratios of oleanolic acid, ursolic acid and betulinic acid compounds in the neuroprotective compositions of the invention. FIG. 8 depicts the HPLC chromatogram of PBI-05204.

EXAMPLE 18

Preparation of Neuroprotective Compositions

Neuroprotective compositions can be prepared by mixing the individual components thereof to form a mixture.
Neuroprotective Composition with Oleandrin and Triterpenes Known amounts of oleandrin, oleanolic acid, ursolic acid and optionally betulinic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP) or mixtures thereof. The resultant mixture contained the components in the relative molar ratios as described herein.

For a pharmaceutically acceptable neuroprotective composition, at least one pharmaceutically acceptable excipient was mixed in with the pharmacologically active agents. A neuroprotective composition is formulated for administration to a mammal.
Neuroprotective Composition with Triterpenes and Excluding Cardiac Glycoside (Oleandrin)

Known amounts of oleanolic acid, ursolic acid and optionally betulinic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP) or mixtures thereof. The resultant mixture contained the components in the relative molar ratios as described herein.

For a pharmaceutically acceptable neuroprotective composition, at least one pharmaceutically acceptable excipient was mixed in with the pharmacologically active agents. A neuroprotective composition is formulated for administration to a mammal.

EXAMPLE 19

Treatment of Neurological Condition Including but not Limited to Alzheimer's Disease Method A. Neuroprotective Composition Therapy A subject presenting with Alzheimer's disease is prescribed neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the neuroprotective composition is continued as needed and the dose or dosing regimen can be adjusted as needed until the patient reaches the desired clinical endpoint.
Method B. Combination Therapy: Neuroprotective Composition and Another Therapeutic Agent Method A, above, is followed except that the subject is prescribed and administered one or more other therapeutic agents for the treatment of Alzheimer's disease, or symptoms thereof. Then one or more other therapeutic agents can be administered before, after or with the extract. Dose escalation (or de-escalation) of the one or more other therapeutic agents can also be done. Suitable one or more other therapeutic agents include Namend™ (memantine HCl), Aricep™ (donepezil), Razadyn™ (galantamine), Exelon™ (rivastigmine), Cognex™ (tacrine), and amantadine.

EXAMPLE 20

Treatment of Neurological Condition Including but not Limited to Huntington's Disease Method A. Neuroprotective Composition Therapy A subject presenting with Huntington's disease is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with neuroprotective composition is continued as needed and the dose or dosing regimen can be adjusted as needed until the patient reaches the desired clinical endpoint. The doses administered can be similar to those described herein.
Method B. Combination Therapy: Neuroprotective Composition and Another Therapeutic Agent Method A, above, is followed except that the subject is prescribed and administered one or more other therapeutic agents for the treatment of Huntington's disease, or symptoms thereof. The one or more other therapeutic agents can be administered before, after or with the neuroprotective composition. Dose escalation (or de-escalation) of the one or more other therapeutic agents can also be done. Suitable one or more other therapeutic agents include Vitamin E, Baclofen (a derivative of CoQ10), Lamotrigine (an anticonvulsant), remacemide (an anesthetic which is a low affinity NMDA antagonist), and riluzole (Na channel blocker).

EXAMPLE 21

Treatment of Neurological Condition Including but not Limited to Ischemic Stroke Method A. Neuroprotective Composition Therapy A subject presenting with ischemic stroke is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the neuroprotective composition is continued as needed and the dose or dosing regimen can be adjusted as needed until the patient reaches the desired clinical endpoint. The doses administered can be similar to those described herein.

Method B. Combination Therapy: Neuroprotective Composition and Another Therapeutic Agent Method A, above, is followed except that the subject is prescribed and administered one or more other therapeutic agents for the treatment of ischemic stroke, or symptoms thereof. The one or more other therapeutic agents can be administered before, after or with the neuroprotective composition. Dose escalation (or de-escalation) of the one or more other therapeutic agents can also be done.

EXAMPLE 22

Treatment of Neurological Condition Including but not Limited to Parkinson's Disease Method A. Neuroprotective Composition Therapy A subject presenting with Parkinson's disease is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with neuroprotective composition is continued as needed and the dose or dosing regimen can be adjusted as needed until the patient reaches the desired clinical endpoint. The doses administered can be similar to those described herein.

Method B. Combination Therapy: Neuroprotective Composition and Another Therapeutic Agent Method A, above, is followed except that the subject is prescribed and administered one or more other therapeutic agents for the treatment of Parkinson's disease, or symptoms thereof. The one or more other therapeutic agents can be administered before, after or with the neuroprotective composition. Dose escalation (or de-escalation) of the one or more other therapeutic agents can also be done. Suitable one or more other therapeutic agents include a combination of carbidopa and levodopa, rasagiline, pramipexole, ropinrole, amantadine, memantine, entacapone, rotigotine, benztropine, selegiline, biperiden, a combination of carbidopa and levodopa and entacapone, trihexylphenidyl, rivastigmine, apomorphine, levodopa, carbidopa, bromocriptine, belladonna, tolcapone, or a combination thereof.

As used herein, the term "about" or "approximately" are taken to mean±10%, ±5%, ±2.5% or ±1% of a specified valued. As used herein, the term "substantially" is taken to mean "to a large degree" or "at least a majority of" or "more than 50% of".

As used herein, the term "and/or", when included in a list is taken to mean the invention includes embodiments including each of the listed items individually or in any combination of any two or more of the listed items.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of treating a neurological condition in a subject comprising: administering to a subject in need thereof a neuroprotective composition comprising oleandrin and at least one triterpene together present in an effective amount to treat said neurological condition, wherein the at least one triterpene is selected from the group consisting of oleanolic acid, ursolic acid, and betulinic acid, and the at least one triterpene is present in free acid form, salt form, derivative form, prodrug form or a combination thereof.

2. The method of claim 1, wherein the molar ratio of oleandrin to total at least one triterpene is about 1:about 9-12, about 1:about 9-11, or about 1:about 9.5-10.5.

3. The method of claim 1, wherein the molar ratio of oleandrin to the at least one triterpene is about 0.5-1.5:about 4-6.

4. The method of claim 2, wherein the at least one triterpene is oleanolic acid or ursolic acid, wherein the at least one triterpene is present in free acid form, salt form, derivative form, prodrug form or a combination thereof.

5. The method of claim 1, wherein at least two triterpenes are present.

6. The method of claim 5, wherein the molar ratio of oleandrin (OL) to the at least two triterpenes (TR) is about 0.5-1.5 OL:about 4-6 TR:about 4-6 TR, or about 0.5-1.5 OL:about 4-6 TR:about 0.1-1 TR.

7. The method of claim 6, wherein the at least two triterpenes include oleanolic acid and ursolic acid or oleanolic acid and betulinic acid, wherein each triterpene is independently present in free acid form, salt form, derivative form, prodrug form or a combination thereof.

8. The method of claim 1, wherein the three triterpenes are present.

9. The method of claim 8, wherein the molar ratio of oleandrin (OL) to the three triterpenes (TR) is about 0.5-1.5 OL:about 4-6 TR:about 4-6 TR:about 0.1-1 TR.

10. The method of claim 1, wherein the total molar amount of triterpene exceeds the molar amount of oleandrin.

11. The method of claim 1, wherein the neurological condition is selected from the group consisting of Alzheimer's disease, Huntington's disease, stroke, and Parkinson's disease.

12. The method of claim 1, wherein the neurological condition is a neurological disease or disorder having an etiology associated with altered Na,K-ATPase activity .

13. The method of claim 1, wherein the neurological condition is a neurological disease or disorder having an etiology associated with altered HIF-1α activity.

14. The method according to claim 1, wherein administration of the neuroprotective composition provides a plasma concentration of oleandrin in the subject in the range of 0.005 to 10 ng/ml.

15. The method according to claim 1, wherein the neuroprotective composition comprises 0.1 to 50 mg of oleandrin.

16. The method according to claim 1, wherein a subject is administered a dose of 12 to 1200 µg of oleandrin.

17. The method according to claim 1, wherein the neuroprotective composition is administered on a recurring basis daily, every other day, every second day, every third day, every fourth day, every fifth day, every sixth day, weekly, every other week, every second week, every third week, monthly, bimonthly, semi-monthly, every other month every second month, quarterly, every other quarter, trimesterly, seasonally, semi-annually, or annually.

18. The method according to claim 1, wherein the neuroprotective composition is administered one or more times in a day.

19. The method according to claim 1, wherein the neurological condition is selected from the group consisting of amyotrophic lateral sclerosis, bovine spongiform encephalopathy, multiple sclerosis, diabetic neuropathy, autism and juvenile neuronal ceroid lipofuscinosis.

20. The method according to claim 1, wherein the neuroprotective composition further comprises one or more other therapeutically effective agents.

21. The method according to claim 20, wherein further comprising:
   a) administering one or more other therapeutic agents selected from the group consisting of BACE inhibitors or acetylcholinesterase inhibitors, when the neurological condition is Alzheimer's disease;
   b) administering one or more other therapeutic agents selected from the group consisting of natural products, anticonvulsants, NMDA (n-methyl d-aspartate receptor antagonists, and sodium channel blockers, when the neurological condition is Huntington's disease; or
   c) administering one or more other therapeutic agents selected from the group consisting of thrombolytic agents, when the neurological condition is stroke-mediated ischemic brain injury or ischemic stroke.

22. A time-delayed method of treating stroke in a subject comprising:
   within an acceptable delay period after a subject has suffered the stroke, administering a neuroprotective composition comprising oleandrin and at least one triterpene together present in an amount sufficient to treat said stroke,
   wherein the at least one triterpene is selected from the group consisting of oleanolic acid, ursolic acid, and betulinic acid, and the at least one triterpene is present in free acid form, salt form, derivative form, prodrug form or a combination thereof.

23. The method according to claim 22, wherein the delay period is 10 hours or less, 8 hours or less, 6 hours or less, 4 hours or less, 3 hours or less, 2 hours or less, 1 hour or less, 45 minutes or less, 30 minutes or less, 20 minutes or less or 10 min or less.

24. The method according to claim 22, wherein the stroke is ischemic stroke or stroke-mediated ischemic brain injury.

25. The method of claim 22, wherein the molar ratio of oleandrin to the at least one triterpene is about 0.5-1.5:about 4-6.

26. The method of claim 25, wherein the at least one triterpene is oleanolic acid or ursolic acid, wherein the at least one triterpene is present in free acid form, salt form, derivative form, prodrug form or a combination thereof.

27. The method of claim 22, wherein at least two triterpenes are present.

28. The method of claim 27, wherein the molar ratio of oleandrin (OL) to the at least two triterpenes (TR) is about 0.5-1.5 OL:about 4-6 TR:about 4-6 TR, or about 0.5-1.5 OL:about 4-6 TR:about 0.1-1 TR.

29. The method of claim 28, wherein the at least two triterpenes include oleanolic acid and ursolic acid or oleanolic acid and betulinic acid, wherein each triterpene is independently present in free acid form, salt form, derivative form, prodrug form or a combination thereof.

30. The method of claim 22, wherein three triterpenes are present.

31. The method of claim 29, wherein the molar ratio of oleandrin (OL) to the three triterpenes (TR) is about 0.5-1.5 OL:about 4-6 TR:about 4-6 TR:about 0.1-1 TR.

32. The method of claim 22, wherein the total molar amount of triterpene exceeds the molar amount of oleandrin.

* * * * *